United States Patent
Arai et al.

(10) Patent No.: US 9,875,394 B2
(45) Date of Patent: Jan. 23, 2018

(54) SKIN ANALYSIS METHOD, SKIN ANALYSIS DEVICE, AND METHOD FOR CONTROLLING SKIN ANALYSIS DEVICE

(71) Applicant: Panasonic Intellectual Property Corporation of America, Torrance, CA (US)

(72) Inventors: Toshiya Arai, Osaka (JP); Masako Ikeda, Osaka (JP); Shinji Uchida, Osaka (JP)

(73) Assignee: Panasonic Intellectual Property Corporation of America, Torrance, CA (US)

( * ) Notice: Subject to any disclaimer, the term of this patent is extended or adjusted under 35 U.S.C. 154(b) by 92 days.

(21) Appl. No.: 14/907,698

(22) PCT Filed: Jul. 28, 2014

(86) PCT No.: PCT/JP2014/003959
§ 371 (c)(1),
(2) Date: Jan. 26, 2016

(87) PCT Pub. No.: WO2015/015793
PCT Pub. Date: Feb. 5, 2015

(65) Prior Publication Data
US 2016/0162728 A1  Jun. 9, 2016

(30) Foreign Application Priority Data

Jul. 31, 2013 (JP) .................................. 2013-158815

(51) Int. Cl.
*G06K 9/00* (2006.01)
*A61B 5/00* (2006.01)
(Continued)

(52) U.S. Cl.
CPC ........ *G06K 9/00281* (2013.01); *A61B 5/1079* (2013.01); *A61B 5/442* (2013.01);
(Continued)

(58) Field of Classification Search
CPC ........... G06K 9/00281; G06K 9/00248; G06K 9/00255; G06K 9/4609; A61B 5/1079;
(Continued)

(56) References Cited

U.S. PATENT DOCUMENTS 9,436,892 B2 *  9/2016  Hu .................... G06K 9/00288
9,565,410 B2 *  2/2017  Huai .................... G06T 5/007
(Continued)

FOREIGN PATENT DOCUMENTS

JP  2007-533391 A  11/2007
JP  2009-003842 A   1/2009
(Continued)

OTHER PUBLICATIONS

International Search Report for corresponding International Application No. PCT/JP2014/003959 dated Oct. 28, 2014.
(Continued)

*Primary Examiner* — Gregory M Desire
(74) *Attorney, Agent, or Firm* — Renner, Otto, Boisselle & Sklar, LLP

(57) ABSTRACT

A control method for controlling a skin analysis device is a control method for controlling a skin analysis device including a camera for obtaining a face image of a subject, a display for displaying the face image of the subject, and a computer, wherein the control method causes the computer of the skin analysis device to execute: obtaining the face image of the subject; determining a target extraction criterion for each of a plurality of skin areas of the face image based on a position on the face image; and extracting a target that satisfies the determined extraction criterion from the
(Continued)

face image; and displaying the extracted target on the display of the skin analysis device.

10 Claims, 22 Drawing Sheets

(51) Int. Cl.
*A61B 5/107* (2006.01)
*G06K 9/46* (2006.01)
*G06T 7/00* (2017.01)
*G06T 11/60* (2006.01)

(52) U.S. Cl.
CPC .............. *A61B 5/448* (2013.01); *A61B 5/743* (2013.01); *A61B 5/748* (2013.01); *A61B 5/7435* (2013.01); *G06K 9/00248* (2013.01); *G06K 9/00255* (2013.01); *G06K 9/4609* (2013.01); *G06T 7/0012* (2013.01); *G06T 11/60* (2013.01); *G06T 2207/30088* (2013.01); *G06T 2207/30201* (2013.01)

(58) Field of Classification Search
CPC ......... A61B 5/442; A61B 5/448; A61B 5/746; G06T 7/0012; G06T 11/60; G06T 2207/30088
See application file for complete search history.

(56) References Cited

U.S. PATENT DOCUMENTS

| | | | | |
|---|---|---|---|---|
| 2004/0218810 | A1* | 11/2004 | Momma | A61B 5/442 382/162 |
| 2005/0025376 | A1* | 2/2005 | Ishida | G06T 5/001 382/254 |
| 2006/0210124 | A1* | 9/2006 | Ishii | G06K 9/00255 382/118 |
| 2006/0274936 | A1* | 12/2006 | Ohkubo | G06K 9/00234 382/167 |
| 2007/0252997 | A1 | 11/2007 | Van Hal et al. | |
| 2007/0258656 | A1 | 11/2007 | Aarabi | |
| 2011/0115786 | A1* | 5/2011 | Mochizuki | G06T 11/001 345/419 |
| 2012/0133753 | A1* | 5/2012 | Chang | G06K 9/00221 348/77 |
| 2012/0288168 | A1* | 11/2012 | Srinivasa | G06K 9/00221 382/118 |
| 2014/0205159 | A1 | 7/2014 | Yoshida | |
| 2016/0162728 | A1* | 6/2016 | Arai | A61B 5/743 382/118 |

FOREIGN PATENT DOCUMENTS

| | | |
|---|---|---|
| JP | 4909686 B2 | 1/2012 |
| WO | WO 2009/142069 A1 | 11/2009 |
| WO | WO 2012/001289 A1 | 1/2012 |
| WO | WO 2013/042436 A1 | 3/2013 |

OTHER PUBLICATIONS

Cula et al., "Assessing facial wrinkles: automatic detection and quantification", Skin Research and Technology 2013; 19; pp. 243-251 (cited in the specification).

Extended European Search Report dated Jun. 24, 2016 for corresponding European Application No. 14832608.5.

* cited by examiner

FIG.8
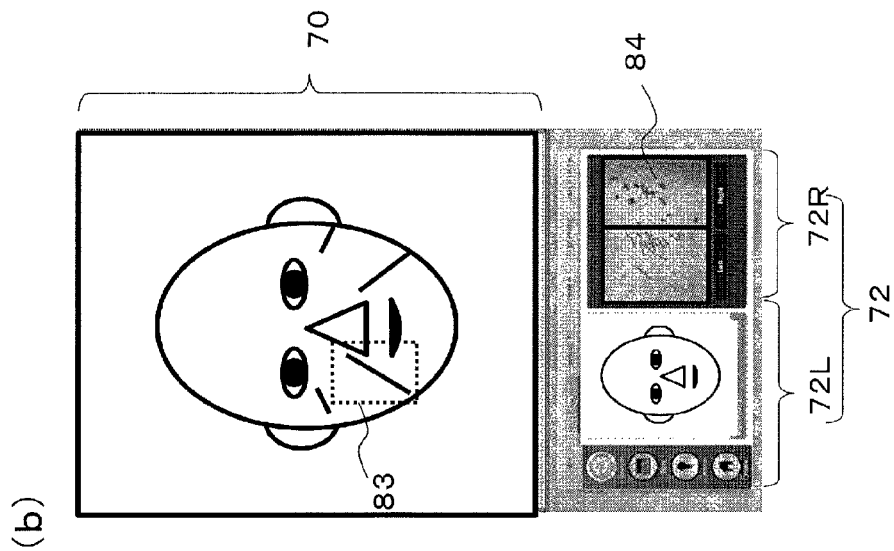
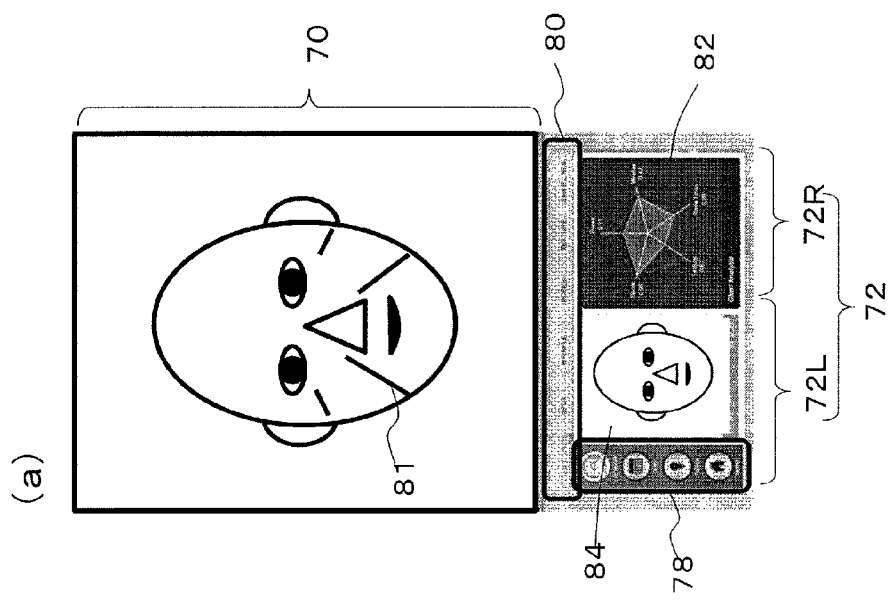

FIG.10
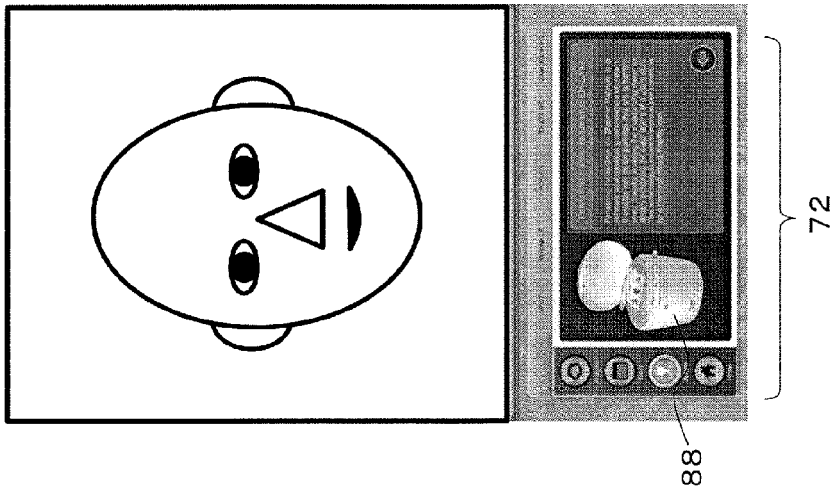
(a)
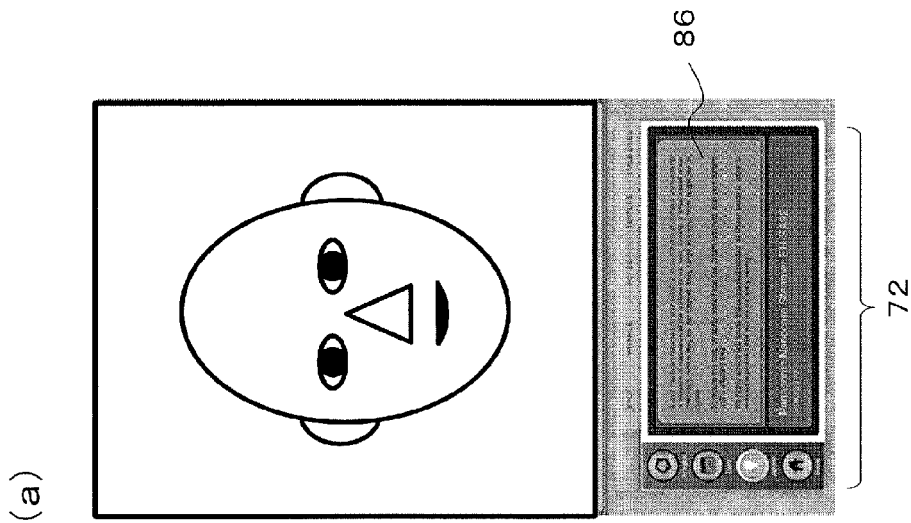
(b)

SKIN ANALYSIS METHOD, SKIN ANALYSIS DEVICE, AND METHOD FOR CONTROLLING SKIN ANALYSIS DEVICE

TECHNICAL FIELD

The present application relates to a skin analysis method, a skin analysis device, and a method for controlling a skin analysis device.

BACKGROUND ART

There are conventional techniques for analyzing the skin condition based on a captured image of the skin so as to visualize and quantify the analysis results. For this, it is necessary to extract objects to be analyzed that are present on the skin surface based on the skin image.

Patent Document No. 1 discloses a technique for extracting skin texture and/or wrinkles from an obtained skin image by performing image processes, including a cross binarization process and/or a short-line segment matching process.

Patent Document No. 2 discloses a technique for extracting skin grooves by converting the brightness values of pixels so that the variance in brightness value of the captured image is greater than or equal to a predetermined value, binarizing each pixel, and performing a matching operation between binarized black pixels and predetermined short-line segments.

Non-Patent Document No. 1 discloses a technique for extracting wrinkles by predetermining the edge direction of the skin based on local features, and performing a filtering process using a Gabor filter having a predetermined orientation.

CITATION LIST

Patent Literature

[Patent Document No. 1] International Publication WO 09/142069
[Patent Document No. 2] Japanese Patent No. 4909686

Non-Patent Literature

[Non-Patent Document No. 1] Cula et al., "Assessing facial wrinkles: automatic detection and quantification", Skin Research and Technology 2013

SUMMARY OF INVENTION

Technical Problem

However, analyzing the skin surface requires troublesome operations or a large device, and analysis based on arbitrary face images is said to require further researches.

Solution to Problem

A control method for controlling a skin analysis device disclosed in the present application is a control method for controlling a skin analysis device, the skin analysis device including a camera for obtaining a face image of a subject, a display for displaying the face image of the subject, and a computer, wherein: the control method causes the computer of the skin analysis device to execute: obtaining the face image of the subject; determining a target extraction criterion for each of a plurality of skin areas of the face image based on a position on the face image; extracting a target that satisfies the determined extraction criterion from the face image; and displaying the extracted target on the display of the skin analysis device.

Advantageous Effects of Invention

According to the skin analysis method and the skin analysis device disclosed in the present application, it is possible to automatically perform, for the entire face, an arbitrary skin wrinkle detection responsive to the user's demand.

BRIEF DESCRIPTION OF DRAWINGS

FIGS. 8(a) and (b) are diagrams each showing an example display screen image to be displayed on the display after skin analysis.

FIGS. 10(a) and (b) are diagrams each showing an example display screen image to be displayed on the display.

Figure 1:
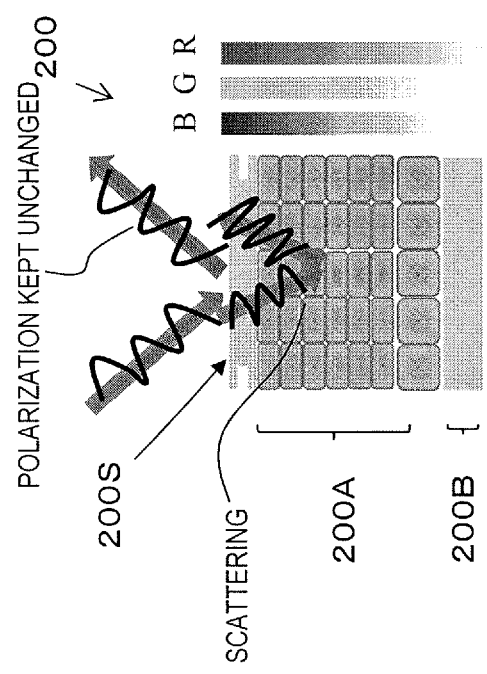
FIG. 1 A diagram schematically showing a structure inside the skin.

DESCRIPTION OF EMBODIMENTS (Findings Forming Basis of the Present Invention)

The technique disclosed in Non-Patent Document No. 1 uses a Gabor filter to extract wrinkles (skin grooves) in the skin image of the user so as to evaluate the skin condition based on the extracted wrinkles. Here, the Gabor filter determines a particular orientation, and extracts wrinkles running toward the determined orientation.

With the technique disclosed in Non-Patent Document No. 1, however, a predetermined portion is cropped from a face image, and the evaluation is performed for the cropped image. Since it is a specialist who crops the image, it is not possible for the user himself/herself to casually evaluate the skin condition from a face image. With the technique disclosed in Non-Patent Document No. 1, the orientation of the Gabor filter is determined based on local features of the image, i.e., the direction on the skin of the user in which wrinkles (skin grooves) are running conspicuously. Therefore, even if the user wishes an evaluation of wrinkles on the nostrils on the face image, for example, conspicuous naso-labial lines may be detected from the face image, i.e., the type of wrinkles detected may not coincide with the type of wrinkles the user wishes to be evaluated.

Particularly, no researches have been undertaken on technical solutions for satisfying the need of each user wishing to have a different type of wrinkles evaluated, depending on the position on the face image of which the skin condition is evaluated.

In view of these problems, the inventors of the present application have arrived at a novel skin analysis method, a novel skin analysis device, and a novel method for controlling a skin analysis device. The skin analysis method, the skin analysis device and the method for controlling a skin analysis device of the present application are outlined below.

one embodiment of a control method for controlling a skin analysis device disclosed in the present application is a control method for controlling a skin analysis device, the skin analysis device including a camera for obtaining a face image of a subject, a display for displaying the face image of the subject, and a computer, wherein: the control method causes the computer of the skin analysis device to execute: obtaining the face image of the subject; determining a target extraction criterion for each of a plurality of skin areas of the face image based on a position on the face image; extracting a target that satisfies the determined extraction criterion from the face image; and displaying the extracted target on the display of the skin analysis device.

In the present embodiment, the control method causes the computer of the skin analysis device to determine a target extraction criterion for each of a plurality of skin areas of the face image based on a position on the face image. Therefore, there is no longer a need for a specialist to perform an operation (cropping a face image) for the skin area analysis of extracting a target, and it is therefore possible for the user to analyze and evaluate the skin area only by preparing a face image.

The control method causes the computer to execute: detecting a face part included in the obtained face image; determining the plurality of skin areas each based on a relative position on the face image with respect to the detected face part; and determining the target extraction criterion for the plurality of skin areas determined. That is, a target extraction criterion is determined based on where the skin area is located in the face image. Therefore, it is possible to extract a target using a different extraction criterion depending on the location of the skin area, e.g., using different extraction criteria for targets around the eyes and for targets around the mouth of the face image, for example.

In the embodiment above, for example, the control method may cause the computer to execute: displaying, on the display, a plurality of target extraction criteria for one of the plurality of skin areas in accordance with the relative position in such a manner that one of the extraction criteria can be selected; when it is determined that one of the plurality of extraction criteria has been selected, extracting a target that satisfies the selected extraction criterion; and displaying the extracted target on the display.

According to the embodiment above, it is possible to evaluate a different type of wrinkles for each user, depending on the position of the skin area on the face image for which the skin condition is to be evaluated.

It is also possible to prevent a problem in which the type of wrinkles detected does not coincide with the type of wrinkles the user desires to be evaluated, e.g., where conspicuous nasolabial lines are detected from the face image even though the user desires to have an evaluation of the nostrils wrinkles on the face image.

In the embodiment above, for example, the target may be a skin groove and/or facial hair.

In the embodiment above, for example, the extraction criterion may be a value representing at least one of an angle, a thickness and a length of the target.

In the embodiment above, for example, the relative position with respect to a face part may be any one of the glabellar area, the under-the-eye area, the lateral canthus area, the medial canthus area, the nose-side area, the mouth area and the forehead, or may be any combination thereof.

In the embodiment above, for example, the extracted target may be displayed on the display while being superimposed over the face image.

In the embodiment above, for example, the target that satisfies the determined extraction criterion may be extracted by a filtering process; and the extraction criterion may be a property of a filter used in the filtering process.

In the embodiment above, for example, the target may be extracted based on a predetermined extraction criterion stored while being associated with a relative position between the face part and the plurality of skin areas.

In the embodiment above, for example, the predetermined extraction criterion may be stored in a memory of the skin analysis device.

In the embodiment above, for example, the predetermined extraction criterion may be stored in a server that can be accessed by the skin analysis device via a network.

In the embodiment above, for example, the number of times one of the plurality of extraction criteria has been selected may be stored in a server that can be accessed by the skin analysis device via a network, and the predetermined extraction criterion may be determined based on a selected frequency.

One embodiment of a skin evaluation method disclosed in the present application includes: obtaining a face image of a subject; determining a target extraction criterion for each of a plurality of skin areas of the face image based on a position on the face image; extracting a target that satisfies the determined extraction criterion from the face image; and displaying the extracted target on a display.

In the embodiment above, for example, the method may include: displaying, on the display, a plurality of target extraction criteria for one of the plurality of skin areas in accordance with the relative position in such a manner that one of the extraction criteria can be selected; when it is determined that one of the plurality of extraction criteria has been selected, extracting a target that satisfies the extraction criterion; and displaying the extracted target on the display.

In the embodiment above, for example, the target may be a skin groove and/or facial hair.

In the embodiment above, for example, the extraction criterion may be a value representing one of an angle, a thickness and a length of the target.

In the embodiment above, for example, the relative position with respect to a face part may be any one of the glabellar area, the under-the-eye area, the lateral canthus area, the medial canthus area, the nose-side area, the mouth area and the forehead, or may be any combination thereof.

In the embodiment above, for example, the target that satisfies the determined extraction criterion may be extracted by a filtering process; and the extraction criterion may be a property of a filter used in the filtering process.

One embodiment of a computer program for controlling a skin analysis device disclosed in the present application is a computer program for controlling a skin analysis device, the skin analysis device including a camera for obtaining a face image of a subject, a display for displaying the image of the subject, and a computer, wherein: the computer program causes the computer of the skin analysis device to execute: obtaining the face image of the subject; determining a target extraction criterion for each of a plurality of skin areas of the face image based on a position on the face image; extracting a target that satisfies the determined extraction criterion from the face image; and displaying the extracted target on the display of the skin analysis device.

This makes it possible to extract a different skin condition depending on the position on the face image that is captured in alignment with a predetermined guide, for example.

In the embodiment above, the computer program causes the computer to execute: detecting a face part included in the obtained face image; determining the plurality of skin areas each based on a relative position on the face image with respect to the detected face part; and determining the target extraction criterion for the plurality of skin areas determined. This makes it possible to extract a different skin condition depending on the position of the face part included in the face image that is captured while the user pays no particular attention to the position.

The extraction criterion is determined based on an updatable database which is predetermined based on the relative position with respect to the face part. This makes it possible to extract based on the tendency of a skin condition that is desired by many users of the skin analysis device.

Targets are extracted based on the extraction criterion selected by the user based on the position in the image. This makes it possible to extract a skin condition that is desired by the currently-operating user.

Thus, according to the above embodiment of the present application, it is possible to automatically perform, for the entire face, the detection of any skin wrinkles in accordance with user requests.

One embodiment of a skin analysis device disclosed in the present application includes: a camera for obtaining a face image of a subject; an extraction criterion determination section for determining a target extraction criterion for each of a plurality of skin areas of the face image based on a position on the face image; a target extraction section for extracting a target that satisfies the determined extraction criterion from the face image; and a display for displaying the extracted target on a display.

In the embodiment above, the skin analysis device further includes a face detection section for detecting a face part included in the face image, and determining the plurality of skin areas each based on a relative position on the face image with respect to the detected face part.

In the embodiment above, the skin analysis device further includes: an extraction criterion selection section for displaying a plurality of extraction criteria related to each of the plurality of skin areas on the display, and accepting one selection; an extraction result evaluation section for converting a target extracted from each of the plurality of skin areas into a score; and a communication section for transmitting the selection result of the extraction criterion selection section and the score to an external server.

The following embodiments each illustrate a specific example of the present invention. Numerical values, shapes, components, steps, orders of steps, etc., to be used in the following embodiments are illustrative and are not to limit the scope of the present invention. Those components introduced in the following embodiments that are not recited in the independent claim(s) representing the most superordinate concept are illustrated herein as optional components. Particulars of any embodiment can be combined with those of any other embodiment.

Embodiment 1

A skin analysis device and a method for controlling the same according to the present embodiment will now be described with reference to the drawings. Each of the skin analysis devices of the embodiments of the present specification captures an image of the face of the subject so as to extract and display skin grooves and facial hair present in a skin area. Skin grooves refer to wrinkles of various lengths, thicknesses and depths, including nasolabial lines. Facial hair includes eyebrows, eyelashes, a mustache and a beard. Skin grooves and facial hair will be referred to as targets. The skin area refers to a selected part of the entire skin including those parts covered by the facial hair.

First, an image-capturing method for capturing an image of the face of the subject and accurately extracting skin grooves and facial hair present in the skin area will be described. FIG. 1 schematically shows a cross section of a human skin. A skin image contains various information such as spots, wrinkles, pores and nasolabial lines on the skin. As shown in FIG. 1, a skin 200 includes an epidermis 200A present in the depth range of about 0.06 mm or more to 0.2 mm toward the inside from a surface 200S of the skin 200, and a dermis 200B present on the inner side of the epidermis 200A. Spots, wrinkles and pores of the skin have different shapes on the skin and are present at different depth positions in the skin 200. Therefore, it is possible to selectively extract skin grooves by obtaining images from different depths of the skin and performing an identification operation based on the shape.

Information of images from different depths of the skin can be obtained by using polarized light or color components. For example, if an image of the skin is captured using linearly-polarized light parallel to a predetermined direction as a light source, the linearly-polarized light is reflected at the surface 200S of the skin while the polarization direction is kept unchanged. On the other hand, linearly-polarized light having been reflected inside the epidermis 200A exits the epidermis 200A with the polarization direction disturbed due to scattering. Thus, if a light source outputting linearly-polarized light is used, and polarized light parallel to the light source is detected (the parallel polarization condition), it is possible to obtain an image with more information from the surface of the skin and less information from the inside of the skin. If a light source outputting linearly-polarized light is used, and polarized light orthogonal to the light source is detected (the orthogonal polarization condition), it is possible to obtain an image with more information from the inside of the skin and less information from the surface of the skin. That is, by using polarized light as the light source, it is possible to obtain an image that selectively includes information from the inside of the skin or information from the surface of the skin.

The longer the wavelength, the further inside of the epidermis 200A light from the light source travels and is reflected. Therefore, of the captured image of the skin, the blue (B) component contains more information from the surface of the skin, and the red (R) and infrared components contain more information from the inside of the epidermis 200A.

A skin groove, being a target, may have a property, such as being able to better absorb light of a particular wavelength region. In such a case, it is possible to accurately extract skin grooves by using light components of that particular wavelength region.

Wrinkles are present in the vicinity of the surface 200S of the skin 200. By performing an image-capturing operation under the parallel polarization condition, with which it is possible to obtain more information from the surface, and obtaining the difference between the blue pixel value and the red pixel value for each pixel of the image, it is possible to obtain an image containing more information of wrinkles while suppressing the influence of reflection of light at the skin surface. By processing an image using a line detection filter such as a Gabor filter, it is possible to obtain an image containing more information of wrinkles and nasolabial lines. For accurately distinguishing between wrinkles and nasolabial lines from each other, one may further perform a threshold process based on the length, the thickness, etc., of the detected portion.

Note that although obtaining the difference between the blue pixel value and the red pixel value has been described above for obtaining an image containing more information of wrinkles, the present invention is not limited to obtaining the difference between the blue pixel value and the red pixel value, and one may obtain only the blue pixel value or may use pixel values of other colors such as green, for example.

Eyebrows, eyelashes, a mustache and a beard typically have a lower color saturation and a lower chromaticity than the skin. Therefore, it is possible to extract eyebrows, eyelashes, a mustache and a beard from the captured image through an image process.

Figure 2:
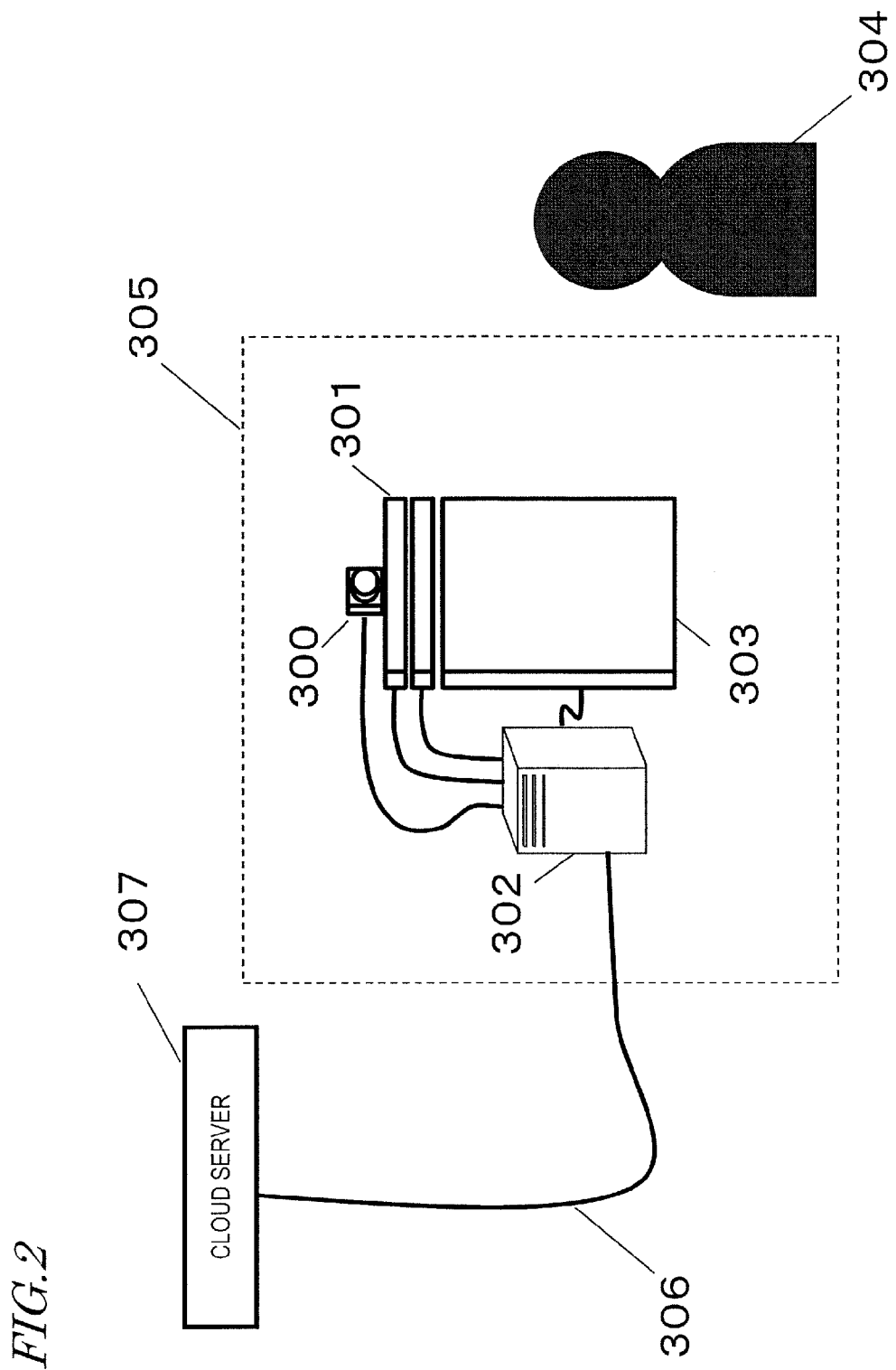
FIG. 2 A diagram showing an overall picture of a skin analysis device according to Embodiment 1 of the present disclosure.

FIG. 2 is a diagram showing an overall picture of a skin analysis device 305 according to the present embodiment. The skin analysis device 305 includes a camera 300, a lighting device 301, a control device 302 and a display 303. Herein, the display 303 preferably includes a touch panel, and the use may be allowed to control the skin analysis device 305 by touching buttons displayed on the display 303 with a finger, or the like.

A face image of a user 304 (subject) received from the camera 300 is obtained by the control device 302 and evaluated by the cloud server 307. Then, skin conditions or indices obtained by quantitatively evaluating the skin conditions are presented on the display 303.

Figure 3:
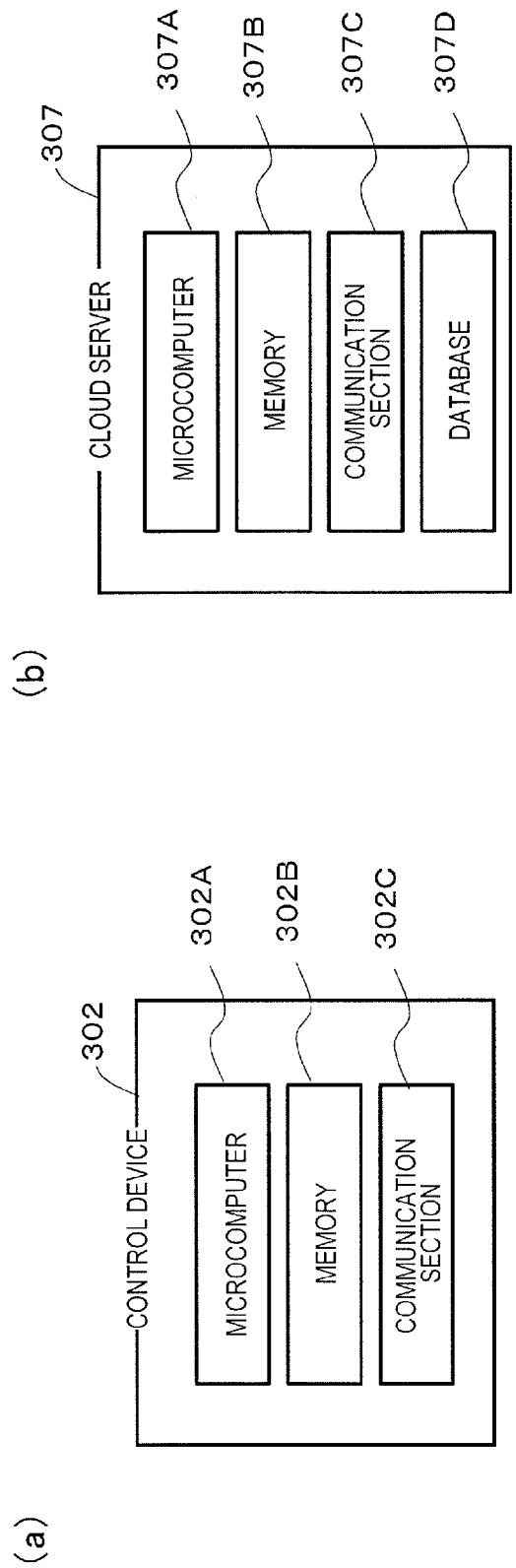
FIG. 3(a) is a diagram showing a configuration of a control device 302, and (b) is a diagram showing a configuration of a cloud server 307.

FIG. 3(a) is a diagram showing a configuration of the control device 302. The control device 302 includes a microcomputer 302A, a memory 302B and a communication section 302C. The microcomputer 302A controls the overall operation of the skin analysis device 305, including operations to be described below. The microcomputer 302A executes various processes to be described below, such as image processes. For example, a computer program for controlling various operations of the skin analysis device 305 is stored in the memory 302B. The microcomputer 302A controls the operation of various components of the skin analysis device 305, such as the camera 300 and the lighting device 301, and executes various processes such as image processes in accordance with the stored computer program.

The camera 300 captures an image of the face of the user 304, obtaining face image data. As described above, in order to accurately extract wrinkles, facial hair, and the like (targets) from the user's face image, the lighting device 301 and the camera 300 may be provided with a polarization filter to thereby obtain images of polarized light. Note that the skin analysis device 305 does not need to include the lighting device 301.

FIG. 3(b) is a diagram showing a configuration of the cloud server 307. The cloud server 307 includes a microcomputer 307A, a memory 307B, a communication section 307C and a database 307D. The cloud server 307 receives, via the communication section 307C, captured images, feature indices of the images, skin evaluation values, etc., from a plurality of skin analysis devices 305. The cloud server 307 stores the various data received from the plurality of skin analysis devices 305 to generate statistical data and obtain correlations between the data. It also transmits, to the skin analysis devices 305, the statistical data and correlations via the communication section 307C.

Note that various processes such as image processes for the face image of the user 304 may be performed on the cloud server 307. The evaluation of the face image of the user 304 may be performed on the control device 302.

Figure 4:
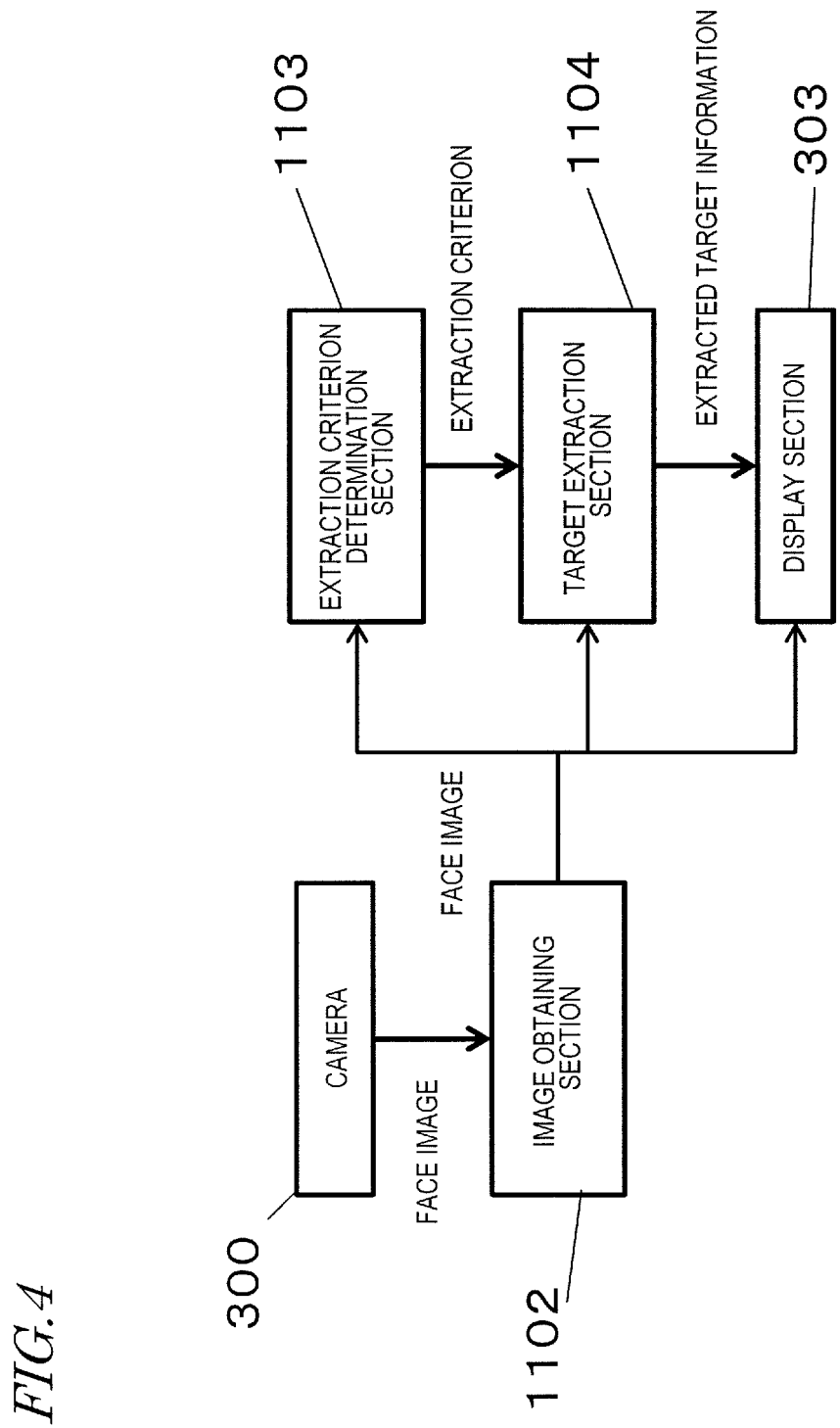
FIG. 4 A functional block diagram of a skin analysis device according to Embodiment 1 of the present disclosure.

FIG. 4 is a block diagram showing a configuration of the skin analysis device 305 according to the present embodiment. The skin analysis device 305 includes the camera 300, an image obtaining section 1102, an extraction criterion determination section 1103, a target extraction section 1104 and the display 303. Note that it may communicate with the cloud server 307 using a communication section (not shown), and the face image evaluation itself may be done on the cloud server 307. The evaluation results may be stored in the cloud server 307.

An operation of the skin analysis device 305 of the present invention will now be described with reference to the drawings.

The skin analysis device 305 of the present embodiment starts its operation with the user 304 being located in front of the camera 300 of the skin analysis device 305.

First, the camera 300 captures an image of the face of the user 304, obtaining the face image. The image obtaining section 1102 receives the face image data from the camera 300 to generate horizontally-inverted face image data. The generated face image data is output to the display 303, and the display 303 displays the horizontally-inverted face image. This is a function as an electronic mirror.

Looking at the face image displayed on the display 303, the user adjusts the position of the face image on the display 303. If the face image of himself/herself is not displayed generally at the center of the display 303, or if the face image is too large or too small, the user moves the position of the face with respect to the camera 300 so that the face image is displayed on the display 303 with a suitable size and at a suitable position. A guide marker, indicating a desirable face position, may be displayed on the display 303 so as to make it easier for the user to adjust the position of the face. In response to the user's instruction to start the image-capturing operation, the skin analysis device 305 starts the operation of analyzing the captured face image.

Figure 5:
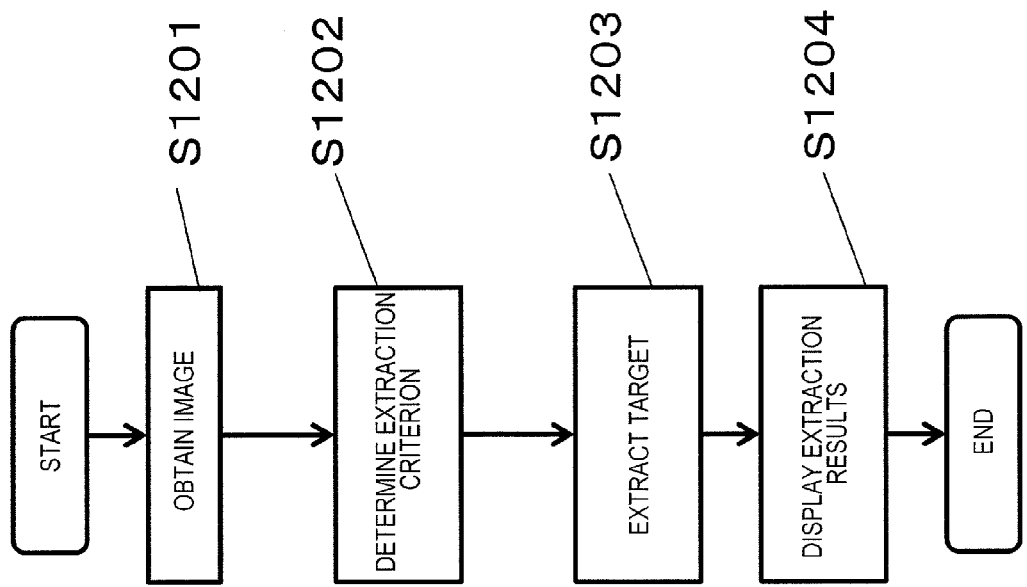
FIG. 5 A flow chart showing a procedure for skin evaluation using a skin analysis device according to Embodiment 1 of the present disclosure.

FIG. 5 is a flow chart showing an operation flow of the skin analysis device 305.

(S1201)

The control device 302 activates the camera 300, allowing the camera 300 to capture an image of the face of the user. The image obtaining section 1102 receives user's face image data from the camera 300 to generate a horizontally-inverted face image. In this process, it is preferred that the lighting device 301 is activated to capture a user's face image under an illuminated condition. The polarization condition and the wavelength of the light to be used are selected depending on the type of targets to be extracted, as described above. If the targets are skin grooves and facial hair, it is possible to obtain an image containing more information of skin grooves and facial hair by performing the image-capturing operation under the parallel polarization condition, with which it is possible to obtain more information from the surface, and obtaining the difference between the blue pixel value and the red pixel value for each pixel of the image.

(S1202)

The extraction criterion determination section 1103 receives the horizontally-inverted face image data from the image obtaining section 1102, and determines the target extraction criterion based on the position on the face image. Herein, an extraction criterion of a target refers to a value representing a feature of the target as will be described in detail below.

(S1203)

The target extraction section 1104 extracts a target from the user's face image based on the target extraction criterion determined in S1202.

(S1204)

The display 303 displays the target extracted in S1203. In this process, the displayed target is preferably displayed while being superimposed over the user's face image.

Figure 6:
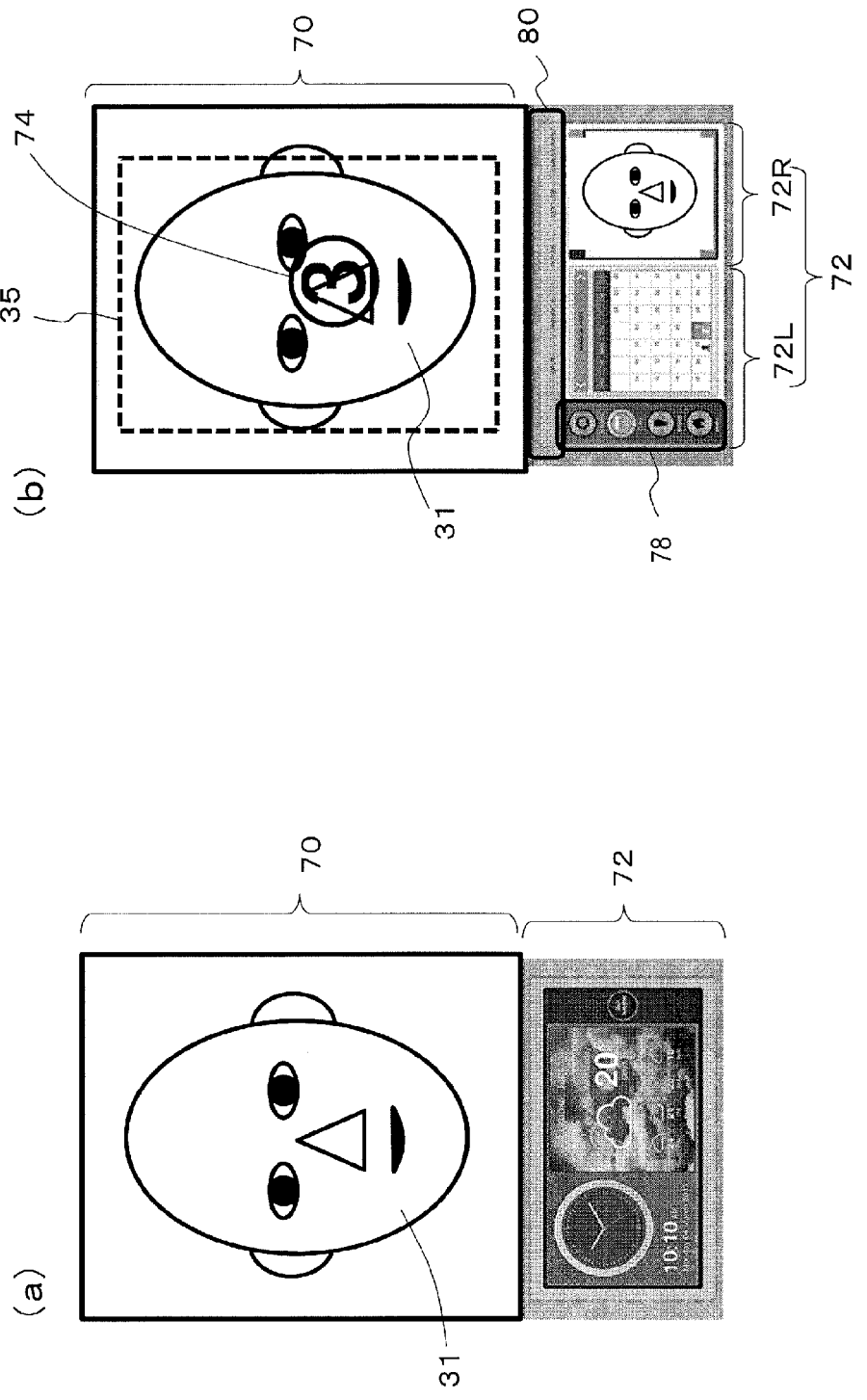
FIG. 6(a) is a diagram showing an example display screen image to be displayed on the display before skin analysis, and (b) is a diagram showing an example display screen image to be displayed on the display during an image-capturing operation.

The operation of the skin analysis device 305 will now be described in greater detail, with reference to illustrative images to be displayed on the display 303. FIG. 6(a) shows an example initial screen image displayed on the display 303 of the skin analysis device 305 before capturing a user's face image. For example, the display area of the display 303 includes the main screen 70 having a large area, and the sub screen 72 having a small area located below the main screen 70. The initial screen includes an image received from the camera 300, which is displayed in real time on the main screen 70, thereby functioning as a digital mirror. Information such as a clock or weather forecast may be displayed, for example, on the sub screen 72.

FIG. 6(b) shows the screen image immediately before the start of an image-capturing operation. A touch panel is provided on the surface of the display 303 as described above, and control menu items and menu items for selecting functions are displayed in the upper portion 80 and the left side portion 78 of the sub screen 72 in response to the user touching the touch panel with a finger, or the like. The main screen 70 may show a guide 35 for guiding the position of the face of the user, for example. A mark indicating the image-capturing timing, a number 74 counting down to the image-capturing operation, etc., may be displayed.

For example, the face image 31 of the user received from the camera 300 is displayed in real time in the right half 72R of the sub screen 72, and a calendar is displayed in the left half 72L. The calendar may include a mark, or the like, indicating that an image was captured in the past using the skin analysis device 305, for example. After the display of FIG. 6(b), an image of the face of the user is captured as described above.

A method for determining the target extraction criterion from the user's face image and a method for extracting a target based on the determined extraction criterion will now be described.

Figure 7:
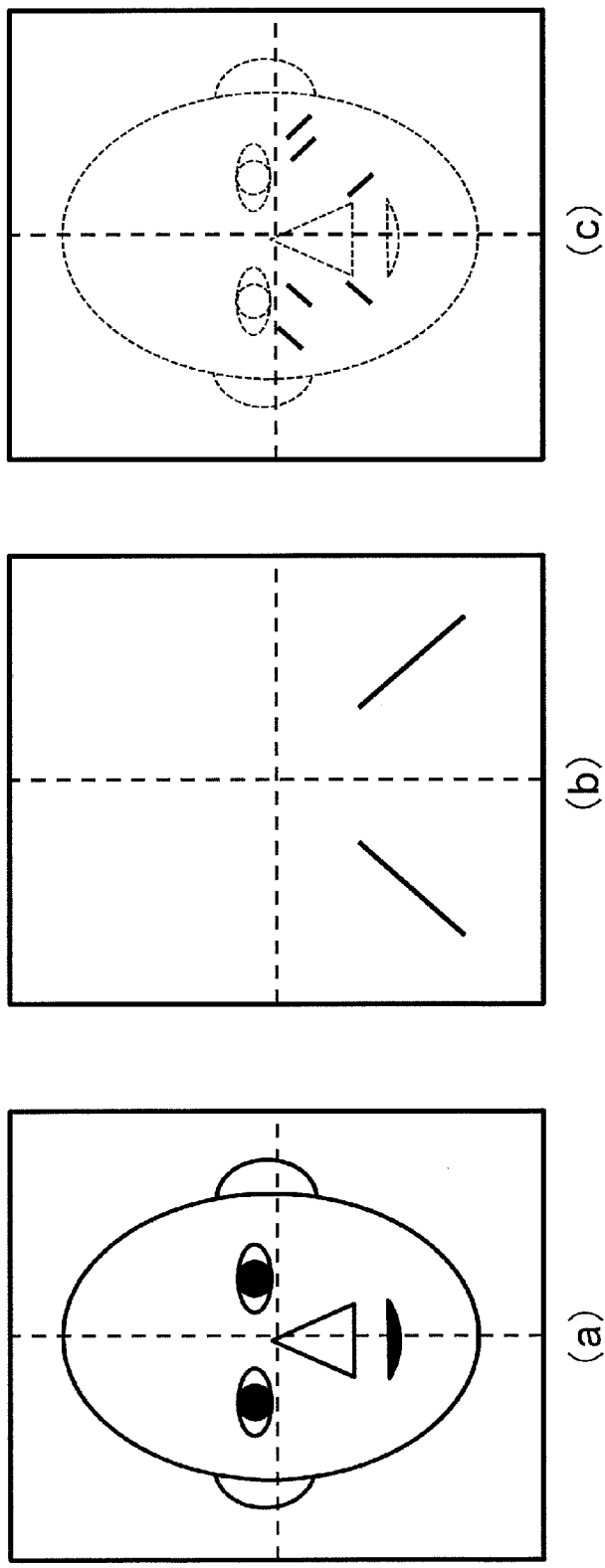
FIGS. 7(a), (b) and (c) are diagrams each schematically showing the process in progress for determining and extracting target features based on their positions on the image.

FIG. 7(a) to (c) are diagrams each schematically showing the process in progress for determining the feature of the target of which the skin condition is to be extracted, based on the position on the user's face image, and extracting the target based on the determined target's feature. In order to determine the extraction criterion of the target based on the position on the face image, the face image is divided into quadrants in the present embodiment, and the extraction criterion is determined for each quadrant. FIG. 7(a) shows the user's face image divided into quadrants, and FIG. 7(b) schematically shows target features as line segments where the target extraction criterion has been determined for each of the third quadrant and the fourth quadrant. The extraction criterion illustrated herein indicates the direction of wrinkles and facial hair (targets). FIG. 7(c) schematically shows wrinkles that have been extracted from the face image based on the determined target feature.

In the target extraction criterion determination step S1202, the user's face image obtained by the image obtaining section 1102 is output to the extraction criterion determination section 1103. The target extraction criterion is determined based on the position on the image as illustrated in FIGS. 7(a) and (b). The extraction criterion is a value representing at least one of the angle, the thickness, the length (size) of the target. For example, in the example shown in FIG. 7(b), no extraction criterion is set for the first and second quadrants, of the four quadrants into which the face image is vertically and horizontally divided. The angle of the target is set as an extraction criterion for the third and fourth quadrants. More specifically, with respect to the boundary between the first quadrant and the fourth quadrant, an angular criterion of 45 degrees is set for the third quadrant, and an angular criterion of −45 degrees (135 degrees) is set for the fourth quadrant. In such a case, the extraction criterion is determined to be within a range of ±10 degrees of the determined angular criterion, for example.

In the target extraction step S1203, the user's face image obtained by the image obtaining section 1102, and the extraction criterion determined by the extraction criterion determination section 1103 are output to the target extraction section 1104. The target extraction section extracts the target based on the user's face image and the target extraction criterion. Specifically, since no extraction criterion is set for the first and second quadrants of the face image, targets satisfying the extraction criterion are not extracted. On the other hand, in the third and fourth quadrants, wrinkles satisfying the extraction criterion described above are extracted. Therefore, as shown in FIG. 7(c), the nasolabial lines and wrinkles under the eyes extending in the same direction as the nasolabial lines are extracted.

When extracting linear targets, such as skin grooves, from the face image, it is not possible to properly extract targets if there is no match for the direction, which is one of the target extraction criteria. For example, the nasolabial line located in the third quadrant of the face image and the nasolabial line in the fourth quadrant extend in different directions from each other, and if an extraction condition suitable for extraction from one quadrant is used, control may fail to properly extract from the other quadrant. According to the present embodiment, it is possible to properly extract wrinkles extending in different directions including the two nasolabial lines since extraction criteria of targets in a plurality of skin areas of the face image are determined based on the positions on the face image.

While wrinkles under the eyes and the nasolabial lines are extracted in the example shown in FIG. 7(c), the thickness of the target may be set as the extraction condition. In such a case, either one of them can be selectively extracted.

The target extraction can be performed by methods using the pattern matching disclosed in Patent Document Nos. 1 and 2, methods using the Gabor filter disclosed in Non-Patent Document No. 1, methods using the Hough transform, etc. Alternatively, a Sobel filter may be used, and other segment extraction methods and filters may be used.

When a Gabor filter is used, for example, parameters such as the x-direction spatial frequency, the y-direction spatial frequency, the filter size, etc., of the filter are determined based on the angular criteria set for the third quadrant and the fourth quadrant described above.

In the extraction result display step S1204, the user's face image obtained by the image obtaining section 1102 and the extraction results for the target extracted by the target extraction section 1104 are output to a display 1105. The display 1105 displays the result screen image as illustrated in FIG. 8(a) and FIG. 8(b) is displayed on the display 303.

In the display example shown in FIG. 8(a), the user's face image used for extracting wrinkles (targets), and extracted targets 81 are displayed on the main screen while being superimposed over the face image. The user's face image is also shown in the left half 72L of the sub screen 72. Menu items for specifying face positions are displayed in an upper portion 80 of the sub screen 72, and menu items for switching between content to be displayed and functions are displayed in the left side portion 78. For example, the user can have a particular skin area of the face displayed and can change content to be displayed by touching the upper portion 80 and the left side portion 78 of the sub screen 72.

FIG. 8(b) shows an example where a portion of the image of the skin area, which is an area 83 designated by the user, is displayed, on an enlarged scale, in the right half 72R of the sub screen 72. Wrinkles (targets) are also displayed in the right half 72R. Targets may be displayed by for example displaying portions of the skin area corresponding to the targets as red areas (lines).

Note that control may not only display the extracted targets, but also evaluate the extracted targets and present the results of the evaluation. For example, where targets are extracted from the face image in accordance with the procedure described above, the evaluation results calculated for the targets are shown in a radar chart, for example, as shown in the right half 72R of the sub screen 72 of FIG. 8(a). For example, control may obtain the density of wrinkles (targets) and display the results of the evaluation.

Moreover, a history of information on the extracted targets and the scores shown in a radar chart may be stored in the control device 302 or the cloud server 307. This allows the user to refer to the evaluation result history at any time, which may be helpful for a chronologically-planned skin care.

Figure 9:
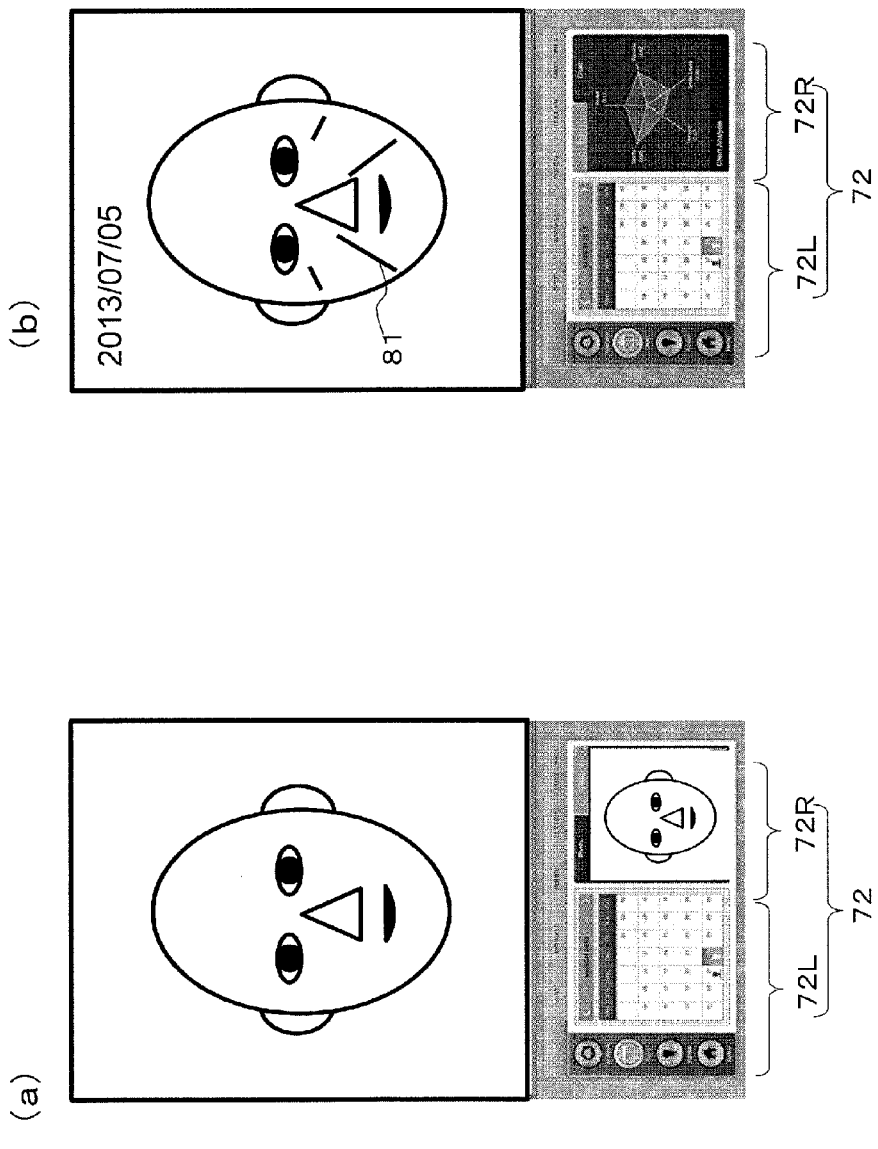
FIGS. 9(a) and (b) are diagrams each showing an example display screen image to be displayed on the display.

For example, a calendar may be displayed on the sub screen 72 as shown in FIG. 9(a). Information is displayed on the calendar that indicates whether or not an evaluation was done for each date. For example, when the user selects a date on the calendar, the past evaluation results as shown in the display example of FIG. 9(b) are displayed on the display 303. In this process, the user's face image, which was evaluated on the selected date, is displayed on the main screen 70, together with the targets which were extracted, and the sub screen 72 displays the calendar together with the extracted targets having been converted into a score, which is shown in a radar chart.

Moreover, based on the evaluation results and the history, there may be presented advice information which is related to skin care optimized for the individual's skin condition and recommended skin care and cosmetic products. As shown in FIG. 10(a), there may be displayed advice which is related to esthetics such as skin treatment based on the evaluation results. Information of cosmetics and beauty appliances for improving the skin condition may also be displayed in detail, as shown in FIG. 10(b).

Embodiment 2

In the present embodiment, control detects a face part included in the face image and determines a skin area based on a relative position with respect to the detected face part so as to set a target extraction criterion.

Figure 11:
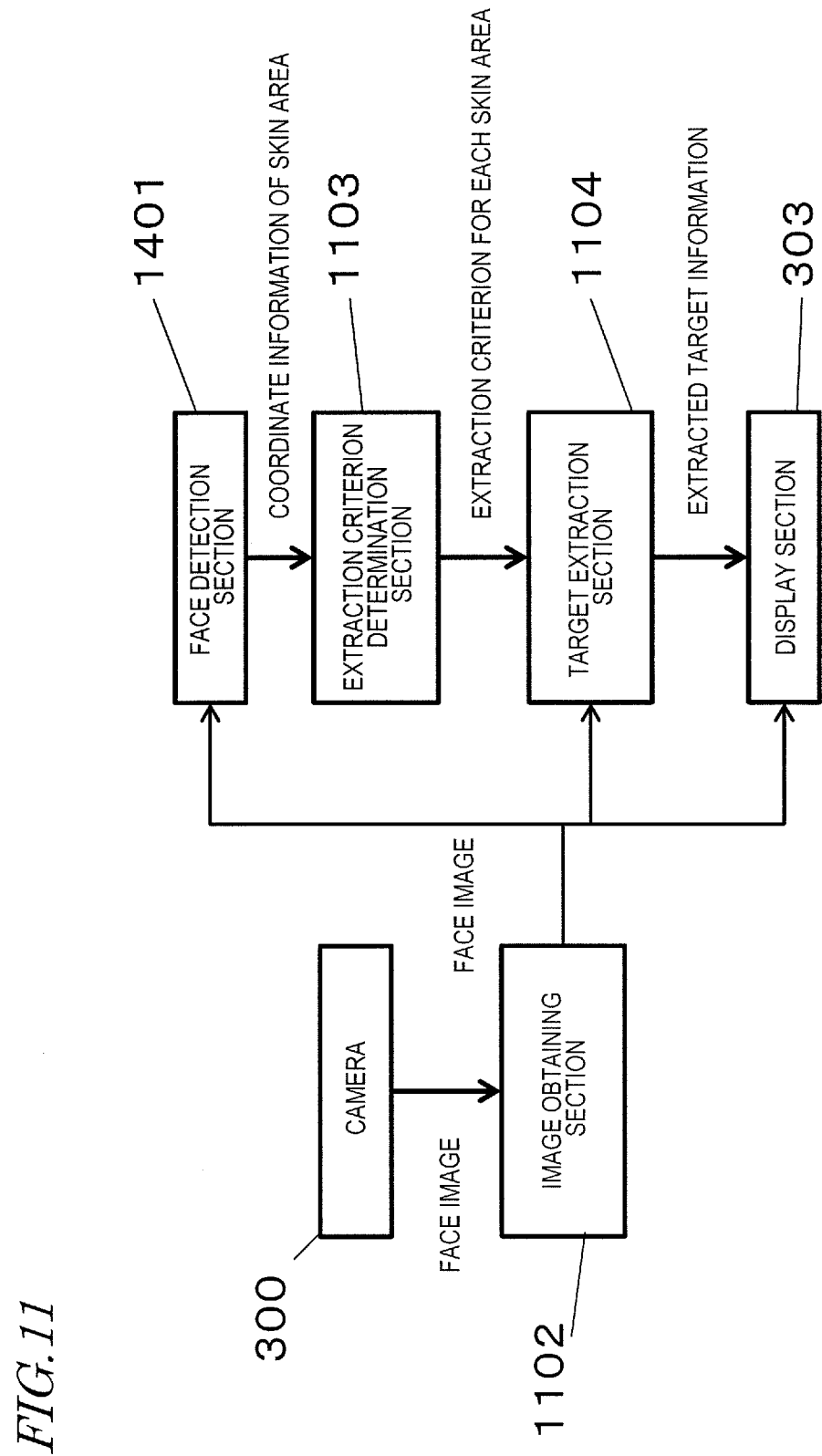
FIG. 11 A functional block diagram of a skin analysis device according to Embodiment 2 of the present disclosure.

FIG. 11 is a block diagram showing a configuration of the skin analysis device 305 according to the present embodiment. A face detection section 1401 is provided, in addition to the configuration of Embodiment 1. The face detection section 1401 detects face parts such as the eyes, the nose, the mouth, the outline, etc., from the user's face image, and determines the coordinates of a plurality of skin areas of the face image based on the relative position with respect to the detected face parts.

Figure 12:
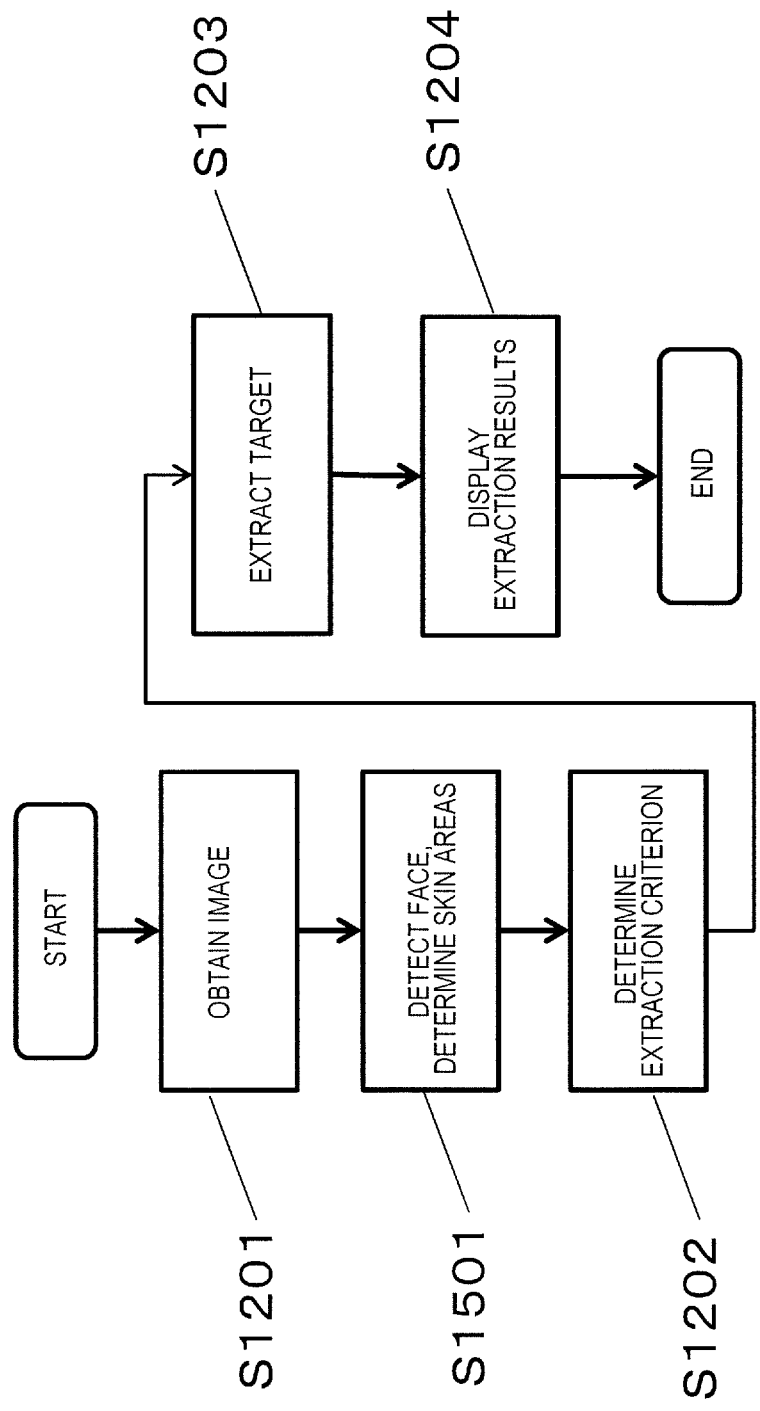
FIG. 12 A flow chart showing a procedure for skin evaluation using a skin analysis device according to Embodiment 2 of the present disclosure.

FIG. 12 is a flow chart showing an operation flow of the skin analysis device 305 according to the present embodiment. The face detection step S1501 is provided, in addition to the operation flow of Embodiment 1.

Figure 13:
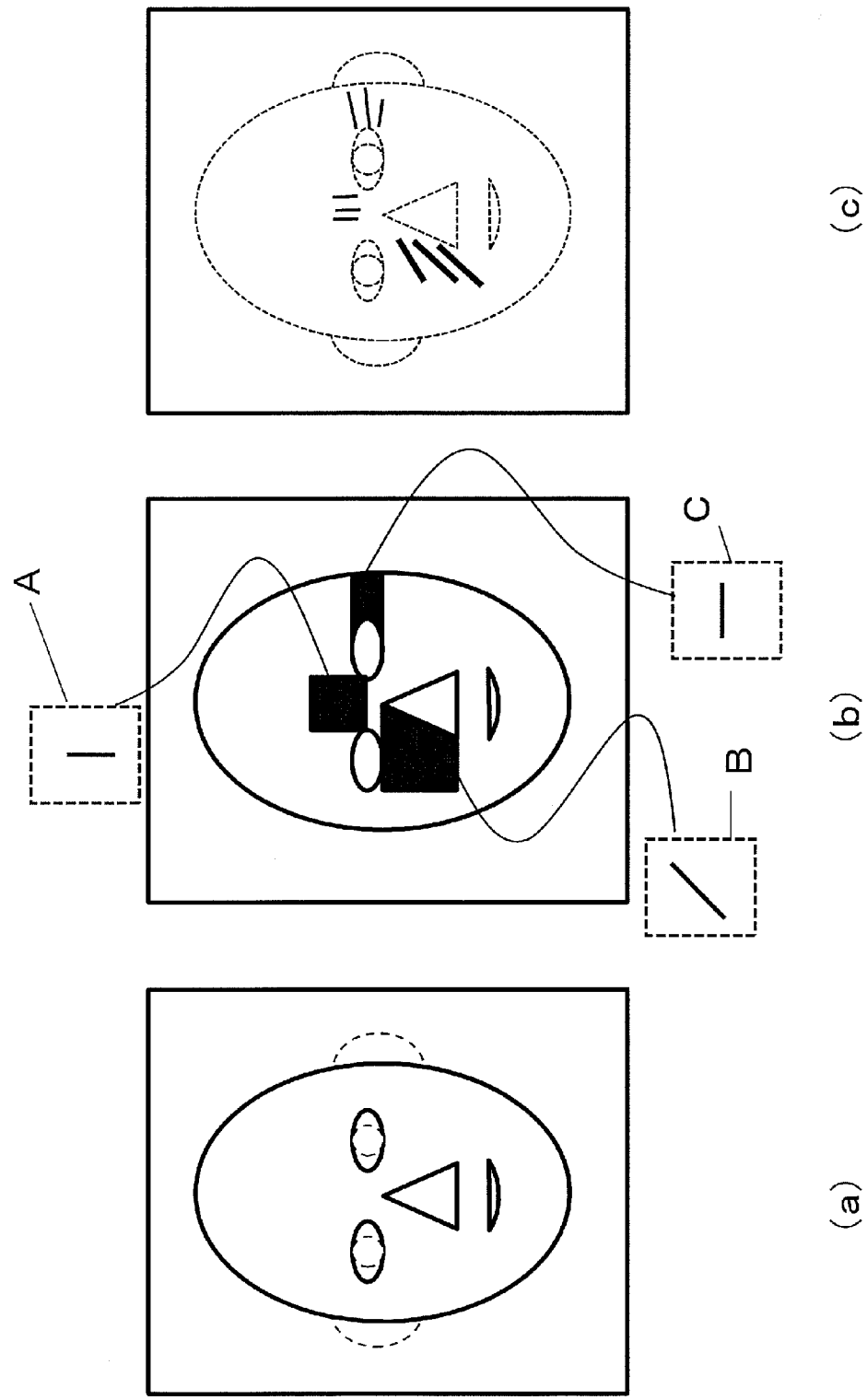
FIGS. 13(a), (b) and (c) are diagrams each schematically showing the process in progress for determining and extracting target features based on a feature point of the face.

FIG. 13 shows a schematic diagram where the target feature is determined based on the face detection position. FIG. 13(a) shows a state where face parts, such as the eyes, the nose, the mouth, the outline, etc., have been detected from the user's face image. The detection of these face parts can be done utilizing known face recognition techniques used in digital cameras, etc. FIG. 13(b) shows how a target extraction criterion is determined for each skin area based on its relative positional relationship with the detected face parts. A skin area defined based on its relative positional relationship with face parts may be, for example, any of the glabellar area, the under-the-eye area, the lateral canthus area, the medial canthus area, the nose-side area, the mouth area and the forehead. It may also be any combination thereof.

For example, the figure shows the orientation of a Gabor filter where targets are extracted by using a Gabor filter. For example, in the skin area A, the orientation of the Gabor filter is set to be a vertical direction, and targets extending along this orientation are extracted. Similarly, the orientation is set to be a lower-left diagonal direction in the skin area B, and the orientation is set to be a horizontal direction across the face in the skin area C. In each area, targets extending along the set orientation are extracted. FIG. 13(c) schematically shows targets (wrinkles) extracted based on the determined target feature.

With reference to FIG. 12, the operation flow of the skin analysis device 305 of the present embodiment will be described.

(S1201)

The control device 302 activates the camera 300, allowing the camera 300 to capture an image of the face of the user. The image obtaining section 1102 receives user's face image data from the camera 300 to generate a horizontally-inverted face image. In this process, it is preferred that the lighting device 301 is activated to capture a user's face image under an illuminated condition. As in Embodiment 1, if the targets are skin grooves and facial hair, it is possible to obtain an image containing more information of skin grooves and facial hair by performing the image-capturing operation under the parallel polarization condition, with which it is possible to obtain more information from the surface, and obtaining the difference between the blue pixel value and the red pixel value for each pixel of the image.

(S1501)

The face detection section 1401 detects face parts, such as the eyes, the nose, the mouth, the outline, etc., from the user's face image. It also determines the coordinates of a plurality of skin areas of the face image based on the relative position with respect to the detected face parts.

(S1202)

The extraction criterion determination section 1103 receives the horizontally-inverted face image data from the image obtaining section 1102 to determine target extraction criteria for the plurality of skin areas.

(S1203)

The target extraction section 1104 extracts a target from the user's face image based on the target extraction criterion determined in S1202.

(S1204)

The display 303 displays the target extracted in S1203. In this process, the displayed target is preferably displayed while being superimposed over the user's face image.

According to the present embodiment, even if the position of the face of the user is somewhat off the camera, it is possible to accurately extract targets from the face image. By setting a different extraction criterion for each skin area, as shown in FIG. 13(b), it is possible to make a distinction such as extracting vertical wrinkles in the glabellar area (the skin area A) while extracting nasolabial lines beside the nose (the skin area B).

Note that a plurality of extraction criteria may be presented to the user for each skin area, and the user may select an extraction criterion for each skin area. Targets are extracted based on the target extraction criterion selected by the user. Now, the plurality of extraction criteria presented to the user are presented for each skin area determined based on the relative position with respect to the face parts detected in the face detection step S1501. For example, in a skin area near a nasolabial line, control may present a target feature for which the orientation of the Gabor filter is a direction along the nasolabial line (a diagonal direction in the image), and a target feature for which the orientation of the Gabor filter is a direction such that small wrinkles of the nose can be extracted.

Embodiment 3

In the present embodiment, control changes the extraction criteria based on the user's selection, and update a database on the cloud server based on the selection history and the skin evaluation results obtained by using the extracted targets, so as to change the selection method and the skin evaluation method.

Figure 14:
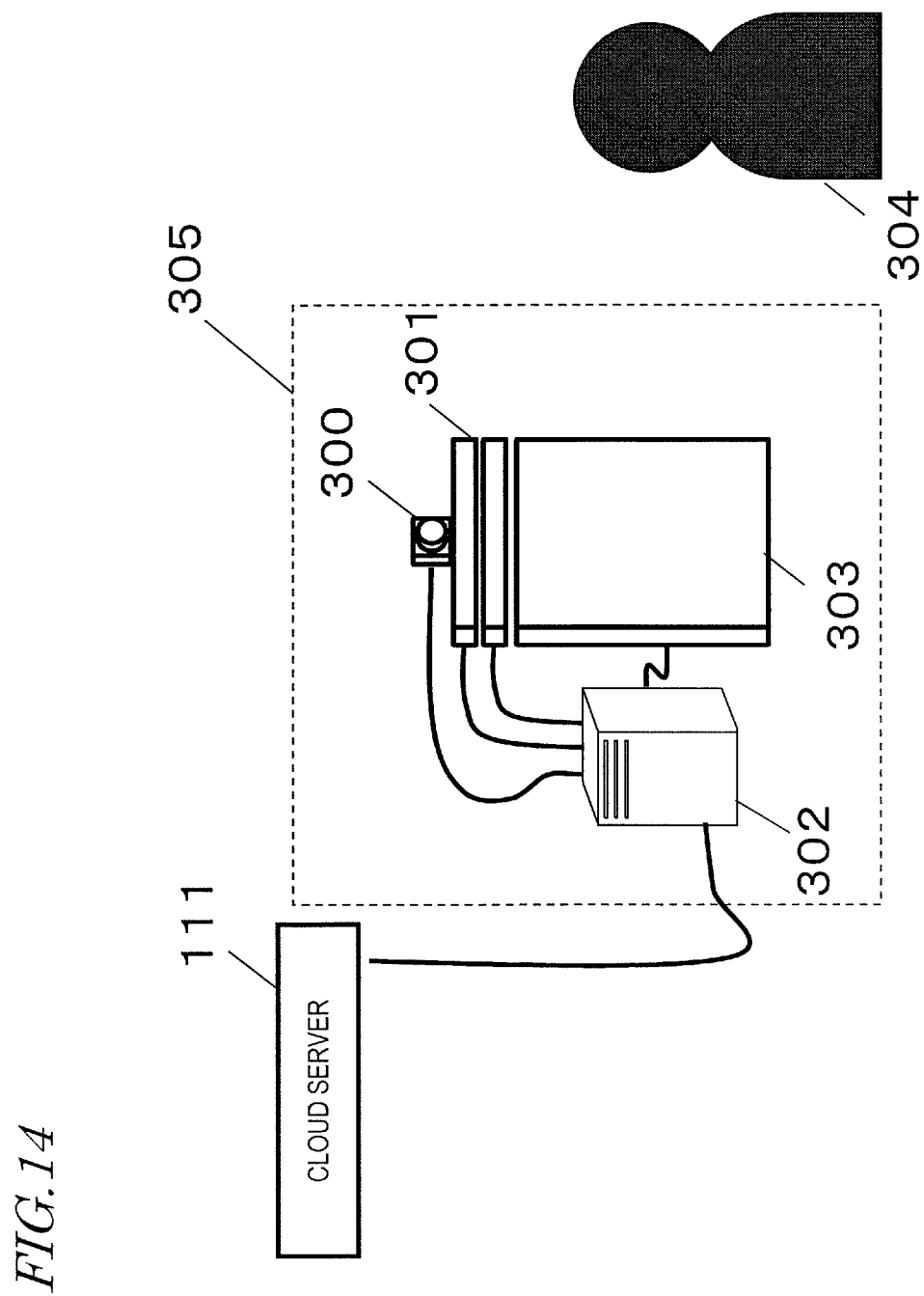
FIG. 14 A diagram showing an overall picture of a skin analysis device according to Embodiment 3 of the present disclosure.

FIG. 14 is a diagram showing an overall picture of a skin analysis device according to the present embodiment. The configuration of a cloud server 111 is different from that of Embodiment 1.

Figure 15:
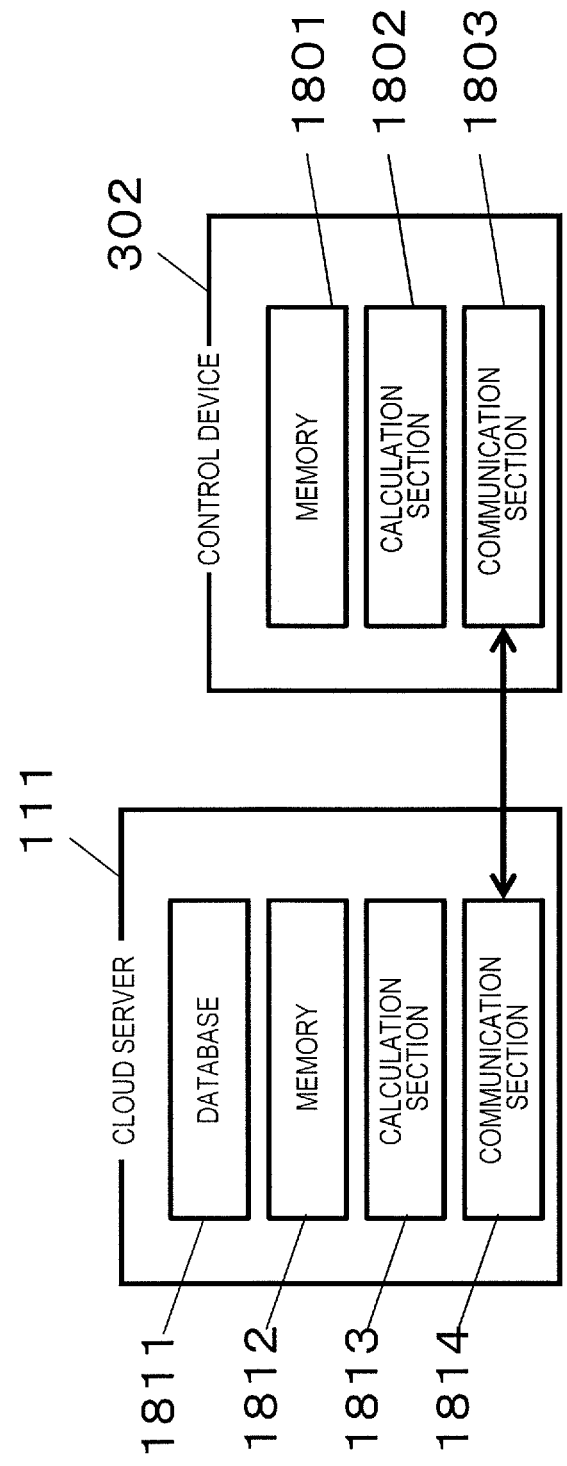
FIG. 15 A diagram showing a configuration of a cloud server and a skin analysis device according to Embodiment 3 of the present disclosure.

FIG. 15 is a diagram showing a configuration of the control device 302 and the cloud server 111. The control device 302 includes a memory 1801, a calculation section 1802 and a communication section 1803. The cloud server 111 includes a database 1811, a memory 1812, a calculation section 1813 and a communication section 1814.

Figure 16:
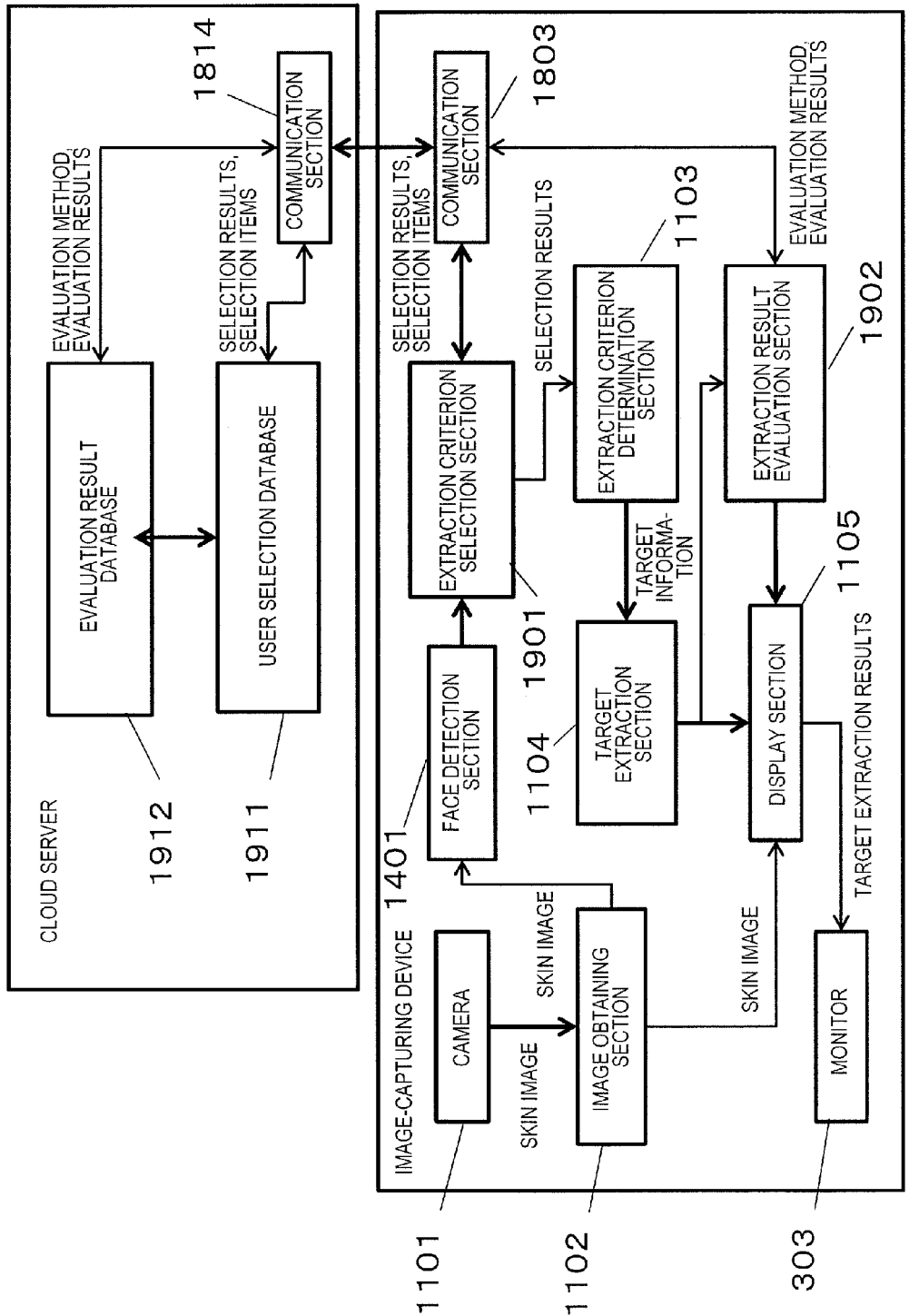
FIG. 16 A functional block diagram of a cloud server and a skin analysis device according to Embodiment 3 of the present disclosure.

FIG. 16 is a block diagram showing a configuration of the skin analysis device 305 and the cloud server 111 according to the present embodiment. The skin analysis device 305 includes an extraction criterion selection section 1901, an extraction result evaluation section 1902 and the communication section 1803, in addition to the configurations of Embodiments 1 and 2. The cloud server 111 includes a user selection database 1911 and an evaluation result database 1912.

The user selection database 1911 accumulates the user selection results, and the evaluation result database 1912 accumulates the skin condition evaluation results based on the extracted targets.

Figure 17:
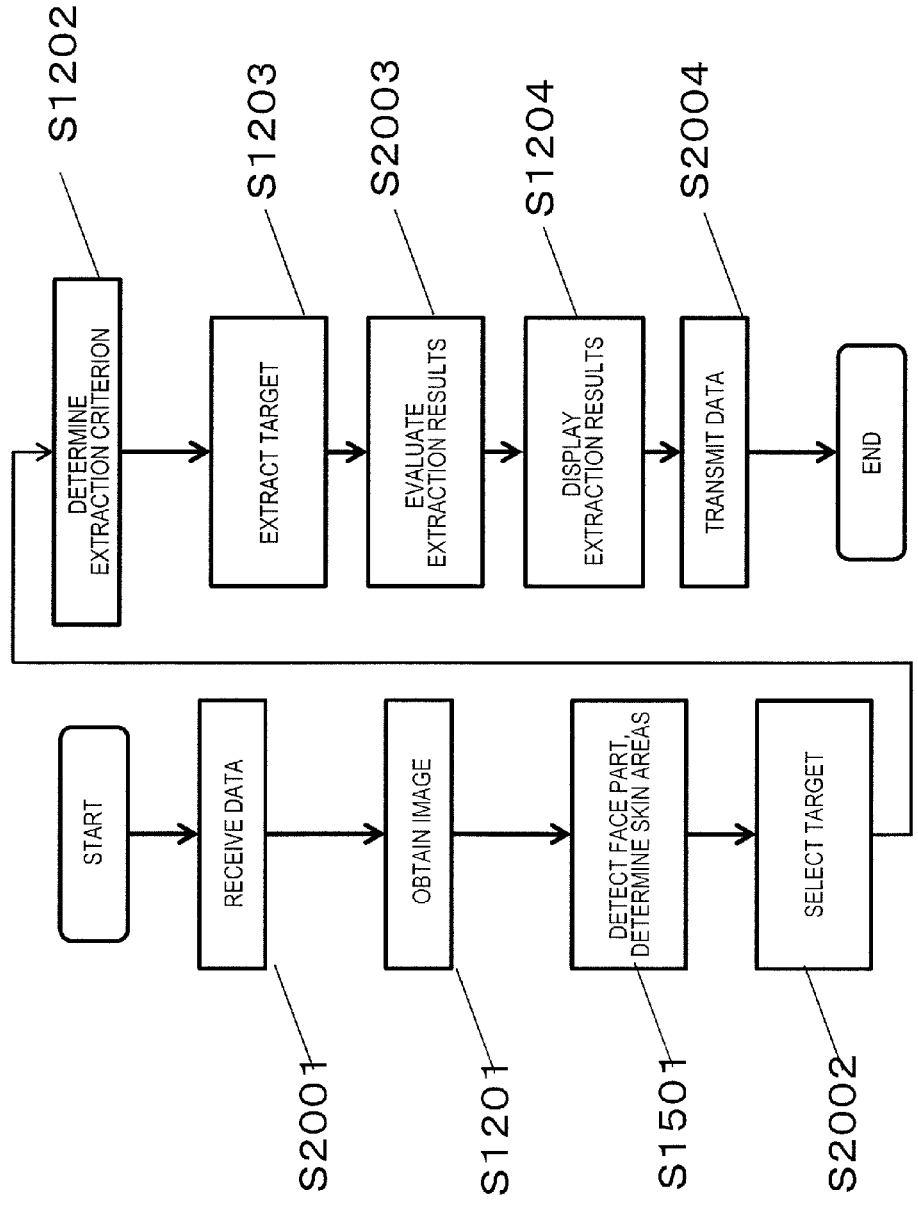
FIG. 17 A flow chart showing a procedure for skin evaluation using a skin analysis device according to Embodiment 3 of the present disclosure.

FIG. 17 is a flow chart showing an operation flow of the skin analysis device 305 according to the present embodiment.

(S2001)

Selection items updated on the user selection database 1911 are transmitted from the communication section 1814 on the cloud server 111 side to the communication section 1803 of the skin analysis device 305, and the selection items of the extraction criterion selection section 1901 are updated.

(S1201)

The control device 302 activates the camera 300, allowing the camera 300 to capture an image of the face of the user. The image obtaining section 1102 receives user's face image data from the camera 300 to generate a horizontally-inverted face image. In this process, it is preferred that the lighting device 301 is activated to capture a user's face image under an illuminated condition. As in Embodiment 1, if the targets are skin grooves and facial hair, it is possible to obtain an image containing more information of skin grooves and facial hair by performing the image-capturing operation under the parallel polarization condition, with which it is possible to obtain more information from the surface, and obtaining the difference between the blue pixel value and the red pixel value for each pixel of the image.

(S1501)

The face detection section 1401 detects face parts, such as the eyes, the nose, the mouth, the outline, etc., from the user's face image. It also determines the coordinates of a plurality of skin areas of the face image based on the relative position with respect to the detected face parts.

(S2002)

The selection items, which are a plurality of extraction criterion related to each of a plurality of skin areas stored in the extraction criterion selection section 1901, are presented on the display 303. The user is allowed to select an extraction criterion for each of a plurality of divided skin areas based on the presented selection items. In this process, it is preferred that for each of the plurality of skin areas, the user is allowed to select an extraction criterion from among a plurality of choices displayed on the display 303.

(S1202)

The extraction criterion determination section 1103 receives the horizontally-inverted face image data from the image obtaining section 1102 to determine target extraction criteria for the plurality of skin areas.

(S1203)

The target extraction section 1104 extracts a target from the user's face image based on the target extraction criterion determined in S1202.

(S2003)

The extraction result evaluation section 1902 converts the extracted targets into a score for each of the plurality of skin areas. The method for calculating the score s1 is as shown below. The calculation is done as shown by the following expression, using the average value a1 extracted from within the range of the selected part and predetermined score conversion coefficients b1 and c1. The calculation of a1 is done by using brightness values of pixels corresponding to the position of the extracted wrinkle, for example.

$$s1 = \frac{a1 - b1}{c1} \quad \text{[Expression 1]}$$

(S1204)

The display 303 displays the target extracted in S1203. In this process, the displayed target is preferably displayed while being superimposed over the user's face image. The score calculated in the extraction result evaluation step S2003 may be displayed on the display 303.

(S2004)

The user selection results from the target selection step are transmitted from the extraction criterion selection section 1901 to the cloud server 111 via the communication section 1803 of the skin analysis device 305, and received by the communication section 1814 of the cloud server 111. The score s1 is transmitted from the extraction result evaluation section 1902 to the cloud server 111 via the communication section 1803 of the skin analysis device 305, and received by the communication section 1814 on the cloud server 111 side.

The cloud server 111 accumulates, in the user selection database 1911, the user selection results of extraction criteria received from a plurality of skin analysis devices 305. The selection items of target extraction criterion are updated based on the tendency from the accumulated selection results from many users. Moreover, based on the user scores s1 and the user selection results received from a plurality of skin analysis devices 305, the analysis ranges, the extraction criteria and the scores s1 are accumulated in the evaluation result database 1912, and the average b2 of the evaluation results of the target features in each analysis range and the variance c2 of the evaluation results are calculated based on the evaluation results from many users.

In the data receiving step 2001, the selection items having been updated based on the user selection database 1911 are transmitted from the communication section 1814 on the cloud server 111 side to the communication section 1803 of the skin analysis device 305, updating the selection items of the extraction criterion selection section 1901. Moreover, the average b2 of the evaluation results and the variance c2 of the evaluation results having been updated based on the evaluation result database 1912 are transmitted from the communication section 1814 of the cloud server 111 to the communication section 1803 of the skin analysis device 305, and the score conversion coefficients b1 and c1 of the extraction result evaluation section are updated based on the average b2 of the evaluation results and the variance c2 of the evaluation results.

What are changed by the method described above are not limited to the selection items of extraction criterion and the average and the variance of the evaluation results, but may also include advice, recommendations, etc., for example. Moreover, coefficients, such as the selection items and the average and the variance of the evaluation results, may be updated based on data of all users, or based on partial data depending on the user's attributes, or based on data of only one user.

The number of times one of a plurality of extraction criteria for each skin area has been selected may be transmitted from the skin analysis device 305 to the cloud server 111 via a network to be stored in the user selection database 1911. As this data is received by a plurality of skin analysis devices 305, the cloud server 111 may obtain the total number of times each extraction criterion has been selected so as to transmit, to each skin analysis device 305, an extraction criterion that has been selected a large number of times. Thus, the skin analysis device 305 can present extraction criteria determined based on the selected frequency to the user as choices.

Embodiment 4

An overall picture of a service to be provided by an information management system including a skin analysis device and a cloud server illustrated in Embodiments 1 to 3 will be described.

Figure 18:
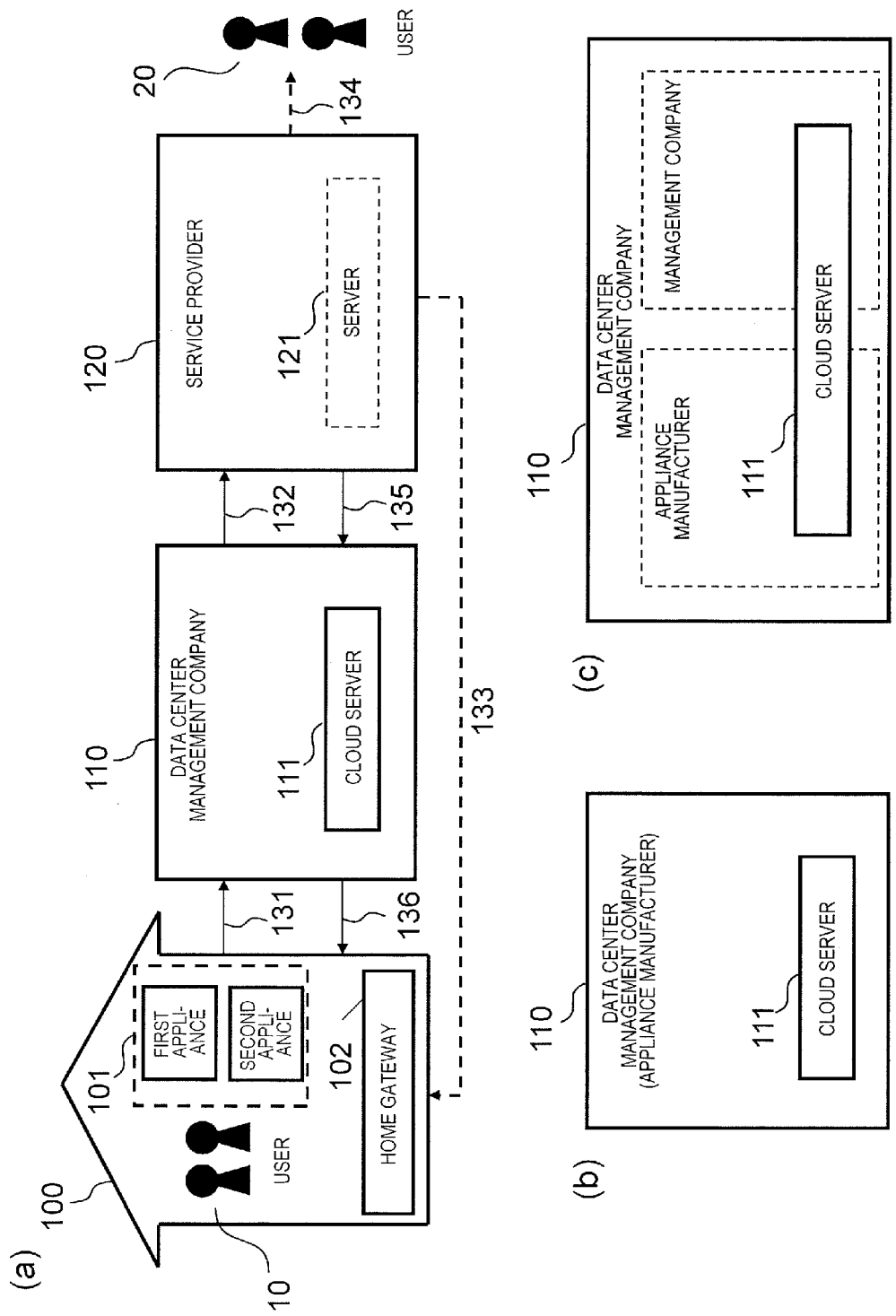
FIG. 18(a) is a diagram showing an overall picture of an information provision system according to Embodiment 4, and (b) and (c) are diagrams each showing a configuration of a data center.

FIG. 18(*a*) is a diagram showing an overall picture of a service provided by an information management system according to the present embodiment. The information management system includes a group 100, a data center management company 110 and a service provider 120.

The group 100 is, for example, a corporate, an organization, a household, etc., whose size is not relevant. The group 100 includes a plurality of appliances 101 and a home gateway 102, the appliances 101 including a first appliance and a second appliance. The plurality of appliances 101 include appliances that can be connected to the Internet (e.g., a smartphone, a personal computer (PC), a television, or the like), and appliances that cannot themselves be connected to the Internet (e.g., a lighting device, a washing machine, a refrigerator, or the like). The plurality of appliances 101 may include appliances that cannot themselves be connected to the Internet but can be connected to the Internet via the home gateway 102. A user 10 uses the plurality of appliances 101 in the group 100. The appliances 101 include a skin analysis device 305 according to one of Embodiments 1 to 3.

The data center management company 110 includes the cloud server 111. The cloud server 111 is a virtualization server that connects with various appliances via the Internet. Primarily, the cloud server 111 manages huge data (big data) that is difficult to handle with an ordinary database management tool, or the like. The data center management company 110 is responsible for management of data, management of the cloud server 111, operation of a data center that is responsible for such management, etc. The details of the services provided by the data center management company 110 will be described later.

Here, the data center management company 110 is not limited to a company that only manages data or manages the cloud server 111. For example, where an appliance manufacturer that develops or manufactures one of the plurality of appliances 101 is responsible for management of data or management of the cloud server 111, etc., as shown in FIG. 18(b), the appliance manufacturer falls under the definition of the data center management company 110. The data center management company 110 is not limited to a single company. For example, where an appliance manufacturer and a management company are responsible for management of data and management of the cloud server 111 either jointly or in such a manner that the operations are divided therebetween, as shown in FIG. 18(c), one or both of them falls under the definition of the data center management company 110.

The service provider 120 includes a server 121. The scale of the server 121 as used herein is not relevant, and the server 121 may be a memory of a personal-use PC, for example. In some cases, the service provider 120 does not include the server 121.

Note that in the information management system described above, the home gateway 102 is not essential. For example, in cases where the cloud server 111 is responsible for all the data management, there is no need for the home gateway 102. There may be no appliances that cannot themselves be connected to the Internet, e.g., where all the appliances in a house are connected to the Internet.

Next, the flow of information in the information management system described above will be described.

First, the first appliance or the second appliance of the group 100 transmits its log information to the cloud server 111 of the data center management company 110. The cloud server 111 accumulates the log information of the first appliance or the second appliance (arrow 131 of FIG. 18(a)). Herein, log information refers to information indicating the status of operation, the date of operation, etc., of the plurality of appliances 101, for example. For example, log information includes a viewing history of a television, recording programming information of a recorder, dates and times of operation of a washing machine, the amounts of laundry of a washing machine, dates and times the door of a refrigerator has been opened and closed, the number of times the door of a refrigerator has been opened and closed, etc. Where the plurality of appliances 101 is the skin analysis device 305 described in Embodiments 1 to 3, log information also includes extraction criteria, etc., described above in Embodiments 1 to 3, in addition to the dates and times of operation of the skin analysis device 305. Log information is not limited to these information, but may also include various information that can be obtained from various appliances. Note that log information may be provided directly from the plurality of appliances 101 themselves to the cloud server 111 via the Internet. Log information may be once sent from the plurality of appliances 101 and accumulated in the home gateway 102, and then provided to the cloud server 111 from the home gateway 102.

Next, the cloud server 111 of the data center management company 110 provides the accumulated log information by a certain unit to the service provider 120. Herein, the certain unit may be a unit by which the data center management company 110 is able to rearrange and provide the accumulated information to the service provider 120, or may be a unit by which the accumulated information is requested by the service provider 120. Although the information is described to be provided by a certain unit, it may not be a certain unit, and the amount of information to be provided may vary depending on circumstances. The log information is stored in the server 121 owned by the service provider 120 as necessary (arrow 132 of FIG. 18(a)).

Then, the service provider 120 rearranges the log information into information that is suitable for the service to be provided to the user, and provides the information to the user. The user to which the information is provided may be the user 10 who uses the plurality of appliances 101, or an outside user 20. As a method for providing information to the user 10, 20, information may be provided for example from the service provider 120 directly to the user 10, 20 (arrows 133 and 134 of FIG. 18(a)). As a method for providing information to the user 10, information may be provided for example to the user 10 after passing again through the cloud server 111 of the data center management company 110 (arrows 135 and 136 of FIG. 18(a)). The cloud server 111 of the data center management company 110 may rearrange the log information into information that is suitable for the service to be provided to the user, and provide the information to the service provider 120.

Note that the user 10 may be different from or the same as the user 20. Note that the techniques described in the embodiments above may be implemented the following types of cloud service, for example. However, types of the cloud service for implementing the techniques described in the embodiments above are not limited thereto.

(Service Type 1: On-Premise Data Center-Type Cloud Service)

Figure 19:
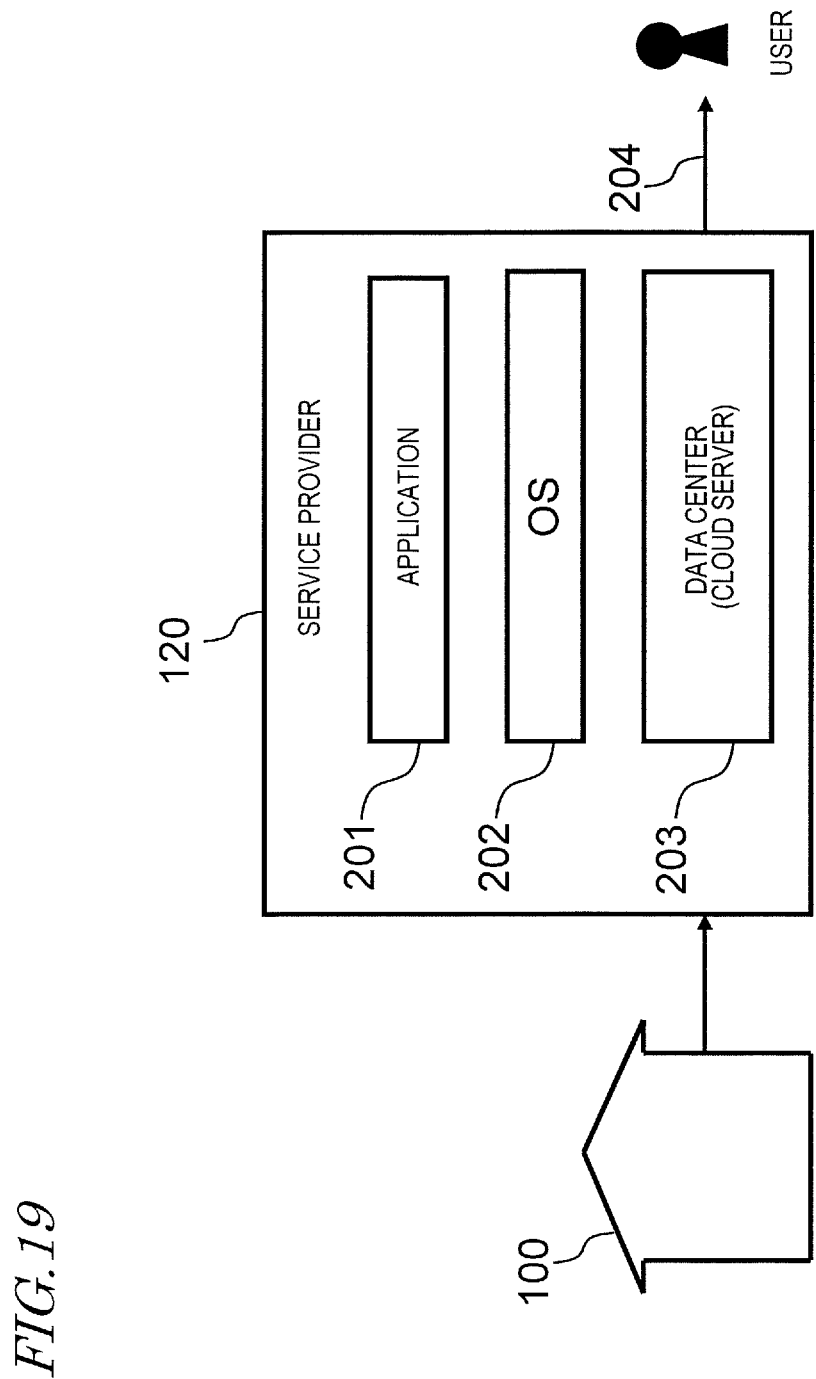
FIG. 19 A diagram showing an overall picture of a service provided by an information management system of service type 1 (on-premise data center-type cloud service).

FIG. 19 is a diagram showing an overall picture of a service provided by an information management system of service type 1 (on-premise data center-type cloud service). In this type, a service provider 120 obtains information from a group 100, and provides a service to the user. In this type, the service provider 120 has the function of a data center management company. That is, the service provider 120 owns a cloud server 203 for managing big data. Therefore, there is no data center management company.

In this type, the service provider 120 operates and manages the data center (cloud server) 203. The service provider 120 manages an operating system (OS) 202 and an application 201. The service provider 120 provides a service (arrow 204) using the OS 202 and the application 201 managed by the service provider 120.

(Service Type 2: IaaS-Based Cloud Service)

Figure 20:
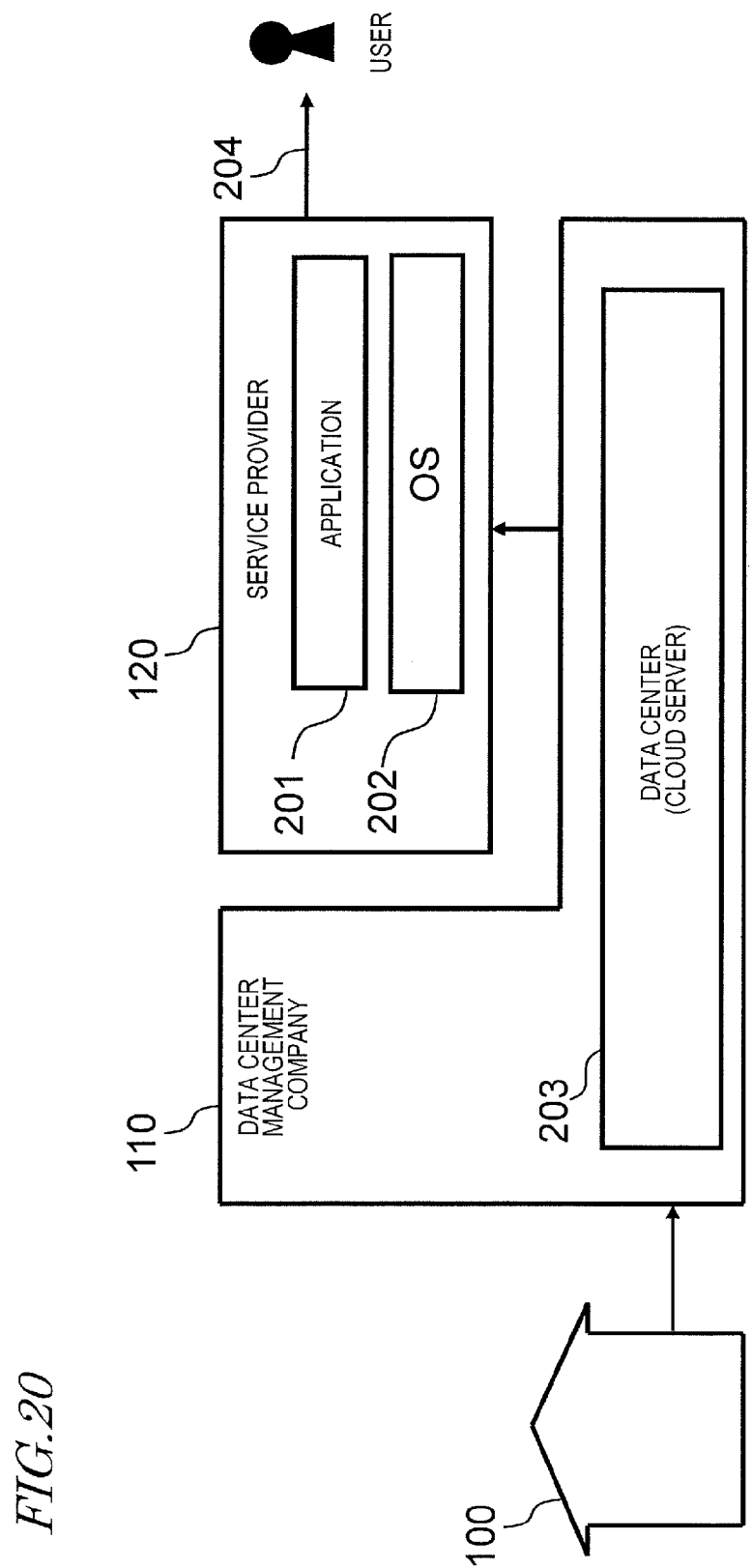
FIG. 20 A diagram showing an overall picture of a service provided by an information management system of service type 2 (IaaS-based cloud service).

FIG. 20 is a diagram showing an overall picture of a service provided by an information management system of service type 2 (IaaS-based cloud service). Herein, IaaS stands for Infrastructure as a Service, referring to a cloud service provision model in which the infrastructure for constructing and running a computing system itself is provided as a service via the Internet.

In this type, a data center management company 110 operates and manages the data center (cloud server) 203. The service provider 120 manages the OS 202 and the application 201. The service provider 120 provides a service (arrow 204) using the OS 202 and the application 201 managed by the service provider 120.

(Service Type 3: PaaS-Based Cloud Service)

Figure 21:
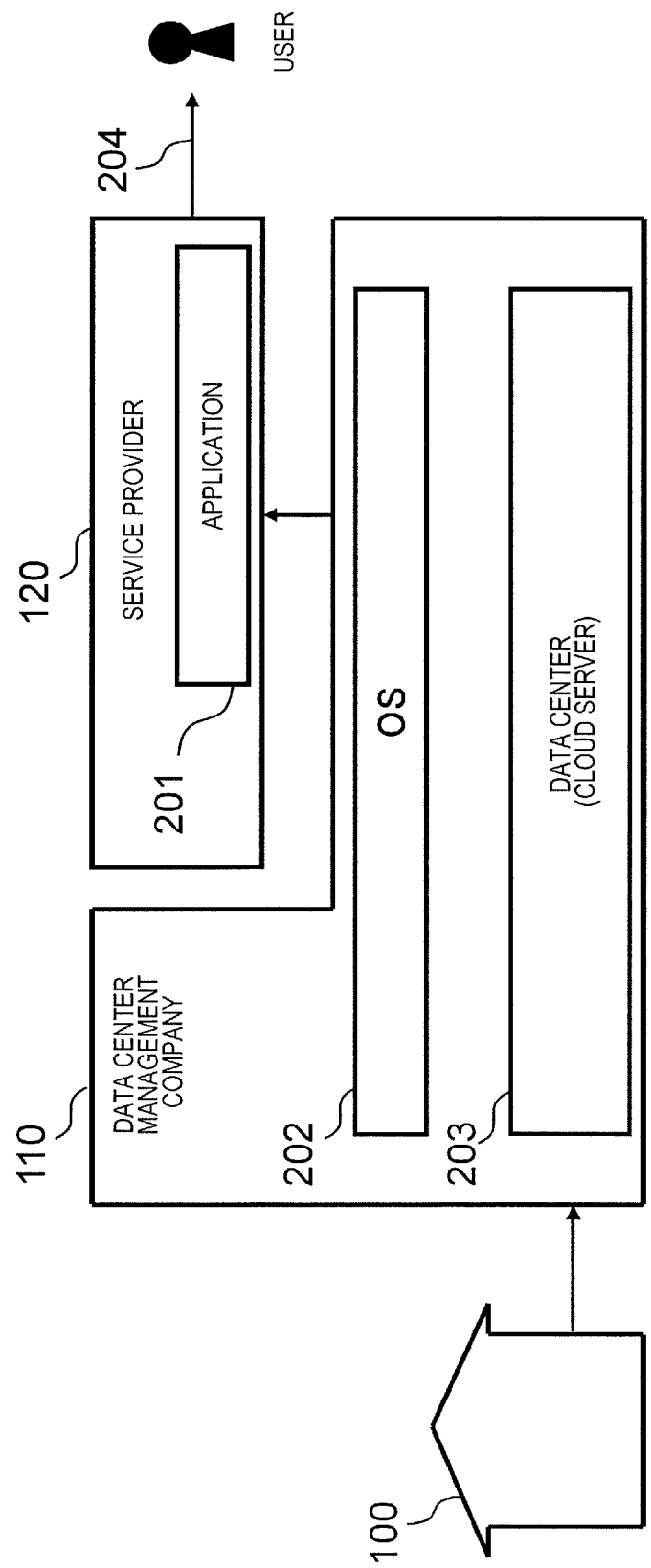
FIG. 21 A diagram showing an overall picture of a service provided by an information management system of service type 3 (PaaS-based cloud service).

FIG. 21 is a diagram showing an overall picture of a service provided by an information management system of service type 3 (IaaS-based cloud service). Herein, PaaS stands for Platform as a Service, referring to a cloud service provision model in which the platform serving as a foundation for constructing and running software is provided as a service via the Internet.

In this type, the data center management company 110 manages the OS 202, and operates and manages the data center (cloud server) 203. The service provider 120 manages the application 201. The service provider 120 provides a service (arrow 204) using the OS 202 managed by the data center management company 110 and the application 201 managed by the service provider 120.

(Service Type 4: SaaS-Based Cloud Service)

Figure 22:
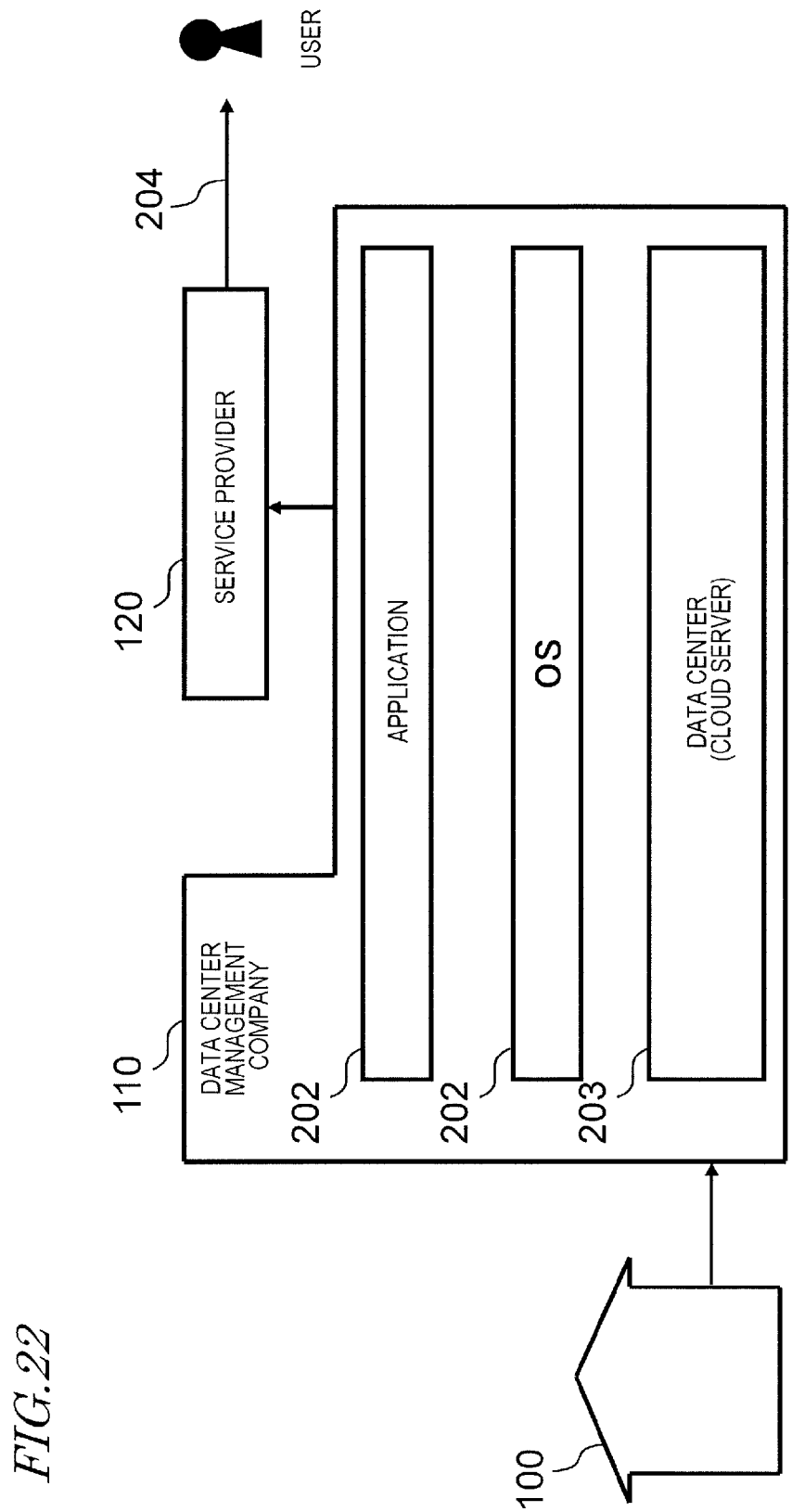
FIG. 22 A diagram showing an overall picture of a service provided by an information management system of service type 4 (SaaS-based cloud service).

FIG. 22 is a diagram showing an overall picture of a service provided by an information management system of service type 4 (SaaS-based cloud service). Herein, SaaS stands for Software as a Service. The SaaS-based cloud service is, for example, a cloud service provision model having a function of allowing applications provided by a platform provider that owns a data center (cloud server) to be used, via a network such as the Internet, by users, such as corporates and individuals, who do not own a data center (cloud server).

In this type, the data center management company 110 manages the application 201, manages the OS 202, and operates and manages the data center (cloud server) 203. The service provider 120 provides a service (arrow 204) using the OS 202 and the application 201 managed by the data center management company 110.

With any of the cloud service types described above, the service provider 120 provides a service. For example, the service provider or the data center management company may develop, by themselves, an OS, an application, a database for big data, etc., or may outsource the development to a third party.

INDUSTRIAL APPLICABILITY

The skin analysis method, the skin analysis device, and the method for controlling a skin analysis device disclosed in the present application can suitably be used in analyzing and evaluating skin areas by means of a skin analysis device.

REFERENCE SIGNS LIST 10, 20 User
31 Face image
35 Guide
70 Main screen
72 Sub screen
72L Left half
72R Right half
74 Number
78 Left side portion
80 Upper portion
81 Target
83 Area
100 Group
101 Appliance
102 Home gateway
105 Display
110 Data center management company
111 Cloud server
120 Service provider
121 Server
200 Skin
200A Epidermis
200B Dermis
200S Surface
201 Application
204 Arrow
300 Camera
301 Lighting device
302 Control device
302A Microcomputer
302B Memory
302C Communication section
303 Display
304 User
305 Skin analysis device
307 Cloud server
307A Microcomputer
307B Memory
307C Communication section
307D Database
330 Display
1102 Image obtaining section
1103 Extraction criterion determination section
1104 Target extraction section
1105 Display
1401 Face detection section
1801 Memory
1802 Calculation section
1803 Communication section
1811 Database
1812 Memory
1813 Calculation section
1814 Communication section
1901 Extraction criterion selection section
1902 Extraction result evaluation section
1911 User selection database
1912 Evaluation result database
2001 Data receiving step

The invention claimed is:

1. A control method for controlling a skin analysis device, the skin analysis device comprising a camera for obtaining a face image of a subject, a display for displaying the face image of the subject, and a computer, wherein:

the control method causes the computer of the skin analysis device to execute:

obtaining the face image of the subject;

detecting a face part included in the obtained face image;

determining a plurality of skin areas each based on a relative position on the face image with resect to the detected face part;

determining a target extraction criterion for each of the determined plurality of skin areas based on a position on the face image, wherein the target extraction criterion comprises a value representing at least one of an angle, a thickness and a length of a target;

performing filtering processing on the face image using a filter to extract one or more targets that satisfy the determined extraction criterion from the face image, wherein the determined extraction criterion is a property of the filter used in the filtering processing;

displaying the one or more extracted targets on the display of the skin analysis device, wherein the one or more extracted targets are displayed on the display while being superimposed over the face image;

displaying, on the display, a plurality of target extraction criteria for one of the plurality of skin areas in accordance with the relative position on the face image with respect to the detected face part in such a manner that one of the extraction criteria can be selected;

when it is determined that one of the plurality of extraction criteria has been selected, performing filtering processing on the face image to extract a target that satisfies the selected extraction criterion, wherein the selected extraction criterion is a property of the filtering processing; and displaying the extracted target on the display, wherein the extracted target is displayed on the display while being superimposed over the face image.

2. The control method according to claim 1, wherein the target is a skin groove and/or facial hair.

3. The control method according to claim 1, wherein the target is extracted based on a predetermined extraction criterion stored while being associated with a relative position between the face part and the plurality of skin areas.

4. The control method according to claim 3, wherein the predetermined extraction criterion is stored in a memory of the skin analysis device.

5. The control method according to claim 3, wherein the predetermined extraction criterion is stored in a server that can be accessed by the skin analysis device via a network.

6. A skin analysis method comprising:
obtaining a face image of a subject;
detecting a face part included in the obtained face image;
determining a plurality of skin areas each based on a relative position on the face image with respect to the detected face part;
determining a target extraction criterion for each of the determined plurality of skin areas based on a position on the face image, wherein the target extraction criterion comprises a value representing at least one of an angle, a thickness and a length of a target;
performing filtering processing on the face image using a filter to extract one or more targets that satisfy the determined extraction criterion from the face image, wherein the determined extraction criterion is a property of the filter used in the filtering processing; and
displaying the one or more extracted targets on a display, wherein the one or more extracted targets are displayed on the display while being superimposed over the face image.

7. The skin analysis method according to claim 6, comprising:
displaying, on the display, a plurality of target extraction criteria for one of the plurality of skin areas in accordance with the relative position in such a manner that one of the extraction criteria can be selected;
when it is determined that one of the plurality of extraction criteria has been selected, performing filtering processing on the face image to extract a target that satisfies the extraction criterion, wherein the selected extraction criterion is a property of the filtering processing; and displaying the extracted target on the display, wherein the extracted target is displayed on the display while being superimposed over the face image.

8. The skin analysis method according to claim 6, wherein the target is a skin groove and/or facial hair.

9. A skin analysis device comprising:
a camera that obtains a face image of a subject;
a processor configure to:
detect a face part included in the obtained face image;
determine a plurality of skin areas each based on a relative position on the face image with respect to the detected face part;
determine a target extraction criterion for each of the determined plurality of skin areas based on a position on the face image, wherein the target extraction criterion comprises a value representing at least one of an angle, a thickness and a length of a target;
perform filtering processing on the face image using a filter to extract one or more targets that satisfy the determined extraction criterion from the face image, wherein the determined extraction criterion is a property of the filter used in the filtering processing; and a display that displays the one or more extracted targets superimposed over the face image, wherein the display displays a plurality of target extraction criteria for one of the plurality of skin areas in accordance with the relative position on the face image with respect to the detected face part in such a manner that one of the extraction criteria can be selected;

the processor performs filtering processing on the face image to extract a target that satisfies a selected extraction criterion when it is determined that one of the plurality of extraction criteria has been selected, wherein the selected extraction criterion is a property of the filtering processing; and the display displays the extracted target superimposed over the face image.

10. The skin analysis device according to claim 9, further comprising:
an extraction criterion selection section that displays a plurality of extraction criteria related to each of the plurality of skin areas on the display, and accepts one selection;
an extraction result evaluation section that converts a target extracted from each of the plurality of skin areas into a score; and
a communication section that transmits the selection result of the extraction criterion selection section and the score to an external server.

* * * * *